(12) United States Patent
Tanabe et al.

(10) Patent No.: US 10,295,678 B2
(45) Date of Patent: May 21, 2019

(54) X-RAY DETECTOR

(71) Applicant: SHIMADZU CORPORATION, Kyoto (JP)

(72) Inventors: Koichi Tanabe, Kyoto (JP); Shingo Furui, Kyoto (JP); Toshinori Yoshimuta, Kyoto (JP); Kenji Kimura, Kyoto (JP); Akihiro Nishimura, Kyoto (JP); Taro Shirai, Kyoto (JP); Takahiro Doki, Kyoto (JP); Satoshi Sano, Kyoto (JP); Akira Horiba, Kyoto (JP); Toshiyuki Sato, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 15/556,557

(22) PCT Filed: Jan. 26, 2016

(86) PCT No.: PCT/JP2016/052192
§ 371 (c)(1),
(2) Date: Sep. 7, 2017

(87) PCT Pub. No.: WO2016/143401
PCT Pub. Date: Sep. 15, 2016

(65) Prior Publication Data
US 2018/0052240 A1     Feb. 22, 2018

(30) Foreign Application Priority Data
Mar. 10, 2015   (JP) .................. 2015-047241

(51) Int. Cl.
*G01T 1/20* (2006.01)
*H01L 27/146* (2006.01)
*A61B 6/00* (2006.01)

(52) U.S. Cl.
CPC .......... *G01T 1/2006* (2013.01); *A61B 6/4241* (2013.01); *G01T 1/20* (2013.01);
(Continued)

(58) Field of Classification Search
CPC ....... G01T 1/2006; G01T 1/20; G01T 1/2018; H01L 27/14689; H01L 27/14629;
(Continued)

(56) References Cited

U.S. PATENT DOCUMENTS

| | | | |
|---|---|---|---|
| 5,712,483 A * | 1/1998 | Boone | G01T 1/1645 250/367 |
| 7,244,943 B2 * | 7/2007 | Seppi | G01T 1/2018 250/367 |

(Continued)

FOREIGN PATENT DOCUMENTS

| | | |
|---|---|---|
| CN | 103026262 A | 4/2013 |
| CN | 103563006 A | 2/2014 |

(Continued)

OTHER PUBLICATIONS

International Search Report and written opinion of the International Searching Authority dated Apr. 12, 2016, in connection with corresponding International Application No. PCT/JP2016/052192. (8 pages).

(Continued)

*Primary Examiner* — Taeho Jo
(74) *Attorney, Agent, or Firm* — Maier & Maier, PLLC

(57) ABSTRACT

A X-ray detector having enhanced X-ray sensitivity, which enables dual energy imaging having high diagnostic performance. This X-ray detector includes: scintillator elements which are partitioned by light blocking walls and which convert low-energy X-rays to light; and scintillator elements which are partitioned by light blocking walls and which convert high-energy X-rays to light. When seen from the (Continued)

direction of incidence of the X-rays, the positional pattern of the light blocking walls and that of the light blocking walls are configured so as not to be in alignment with each other. Accordingly, the X-rays incident on the X-ray detector are converted to light by at least either one of the scintillator elements and are finally outputted as X-ray detection signals.

9 Claims, 19 Drawing Sheets

(52) U.S. Cl.
CPC ...... G01T 1/2018 (2013.01); H01L 27/14634 (2013.01); H01L 27/14638 (2013.01); *H01L 27/14629* (2013.01)

(58) Field of Classification Search
CPC ......... H01L 27/14658; H01L 27/14676; H01L 27/14692; H01L 27/14634; H01L 27/14638; A61B 6/4241
USPC .................................... 250/370.11
See application file for complete search history.

(56) References Cited

U.S. PATENT DOCUMENTS

| | | | | |
|---|---|---|---|---|
| 7,635,848 | B2* | 12/2009 | Nelson | G01T 1/2002 250/370.11 |
| 2002/0064252 | A1* | 5/2002 | Igarashi | A61B 6/06 378/19 |
| 2002/0110216 | A1* | 8/2002 | Saito | G01N 23/046 378/19 |
| 2004/0251420 | A1* | 12/2004 | Sun | G01T 1/2018 250/370.09 |
| 2007/0138409 | A1* | 6/2007 | Daniel | G01T 1/20 250/483.1 |
| 2008/0011960 | A1* | 1/2008 | Yorkston | G01T 1/2018 250/370.09 |
| 2008/0128631 | A1* | 6/2008 | Suhami | G01T 5/02 250/370.09 |
| 2008/0245968 | A1* | 10/2008 | Tredwell | G01T 1/2018 250/370.09 |
| 2011/0080995 | A1* | 4/2011 | Hoffman | A61B 6/032 378/19 |
| 2012/0145911 | A1* | 6/2012 | Suyama | G01V 5/005 250/366 |
| 2012/0153163 | A1 | 6/2012 | Levene et al. | |
| 2012/0294421 | A1* | 11/2012 | Mukaide | G01N 23/04 378/62 |
| 2013/0022169 | A1* | 1/2013 | Iwasaki | G01T 1/202 378/62 |
| 2013/0126743 | A1* | 5/2013 | Iwakiri | A61B 6/4216 250/366 |
| 2013/0126850 | A1* | 5/2013 | Iwakiri | H01L 51/0001 257/40 |
| 2013/0292574 | A1* | 11/2013 | Levene | G01T 1/2018 250/362 |
| 2014/0037045 | A1* | 2/2014 | Dafni | A61B 6/032 378/5 |
| 2014/0044234 | A1* | 2/2014 | Hashimoto | A61B 6/4291 378/62 |
| 2014/0091235 | A1 | 4/2014 | Iguchi et al. | |
| 2014/0332668 | A1* | 11/2014 | Nishihara | H04N 5/32 250/208.1 |
| 2015/0323685 | A1* | 11/2015 | Nelson | G01T 1/1611 250/370.08 |
| 2015/0331117 | A1* | 11/2015 | Ho | G01T 1/2004 250/367 |
| 2017/0059721 | A1* | 3/2017 | Simanovsky | G01T 1/2018 |

FOREIGN PATENT DOCUMENTS

| | | | |
|---|---|---|---|
| EP | 3067332 | A4 * | 5/2017 |
| JP | 1-191085 | A | 1/1989 |
| JP | 11-505142 | A | 5/1999 |
| JP | 2012-026979 | A | 2/2012 |
| JP | 2013-504057 | A | 2/2013 |
| WO | 2011/033841 | A1 | 3/2011 |
| WO | 2012014874 | A1 | 2/2012 |
| WO | 2012161304 | A1 | 11/2012 |

OTHER PUBLICATIONS

Office Action dated Dec. 26, 2018 in corresponding Chinese Application No. 201680014450.3; 11 pages including English-language translation.

* cited by examiner

[Fig. 1]
(a)
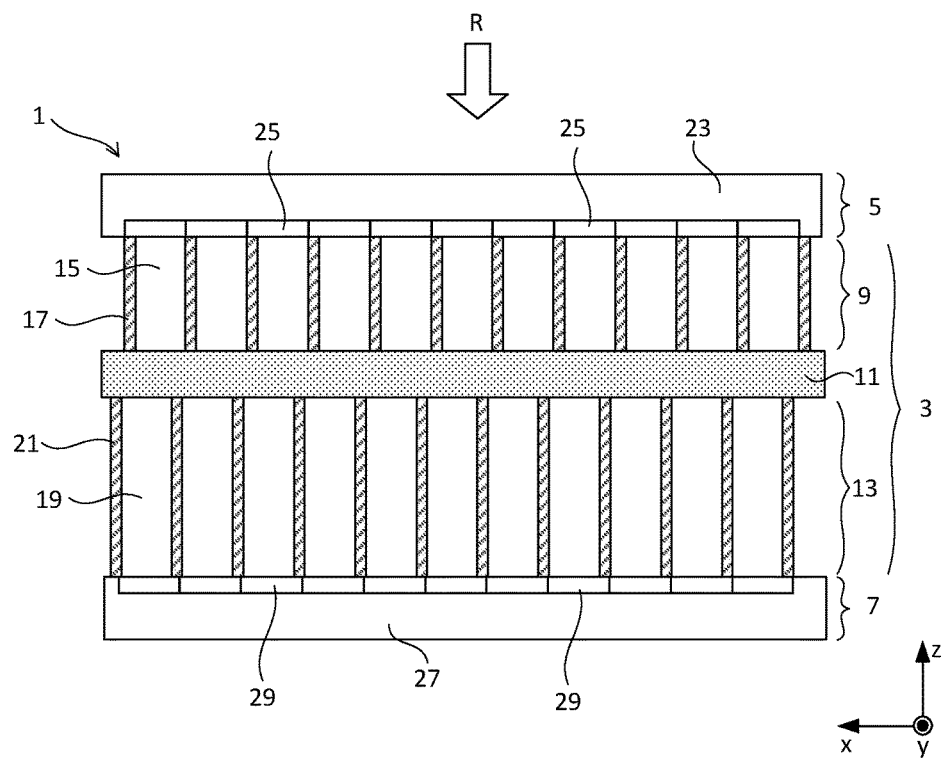
(b)
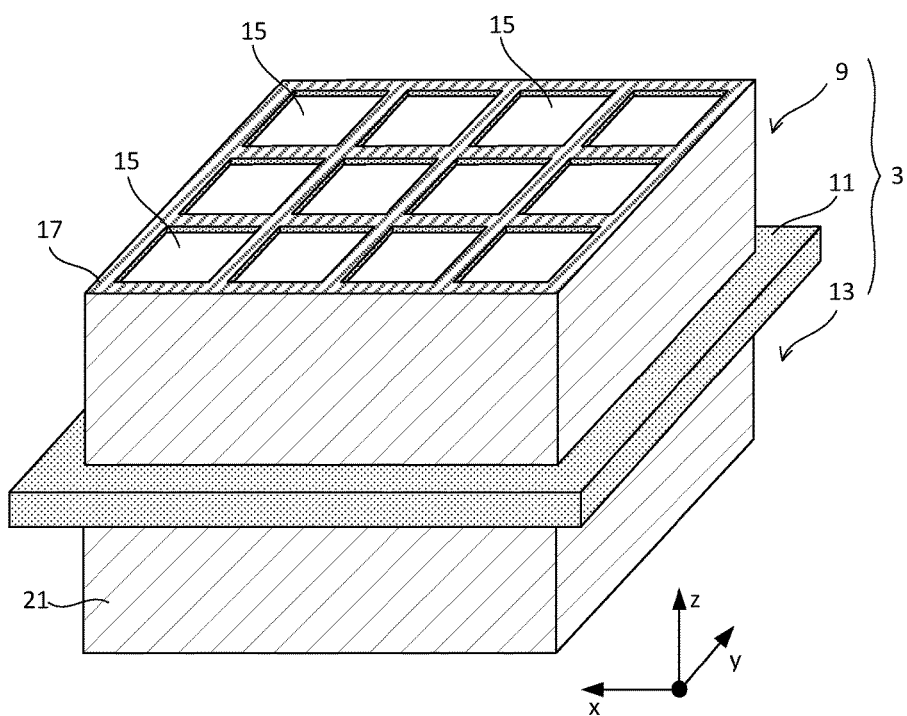

[Fig. 2]
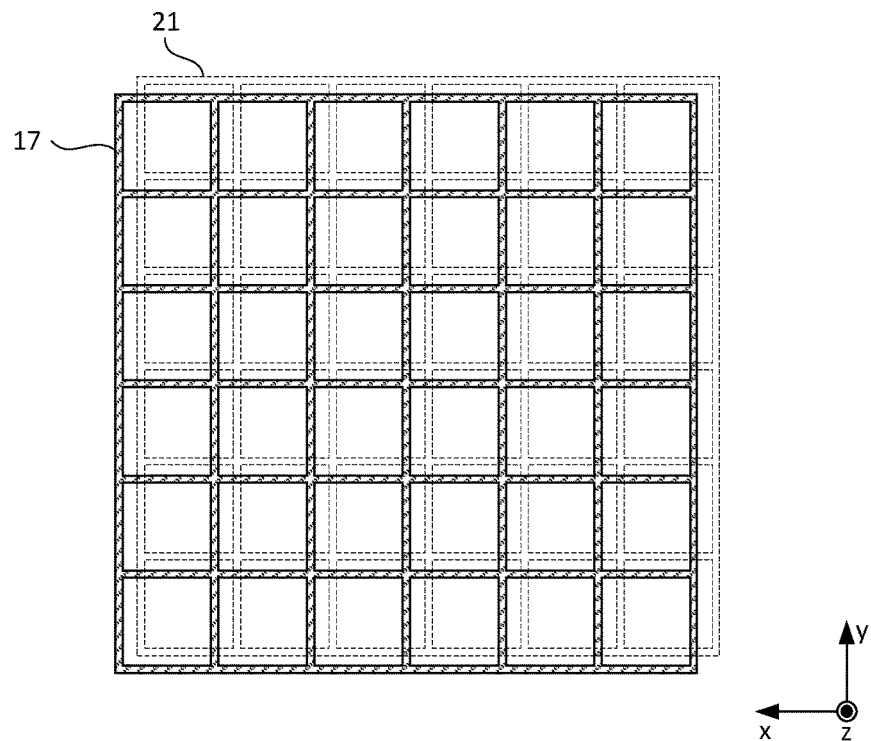
[Fig. 3]
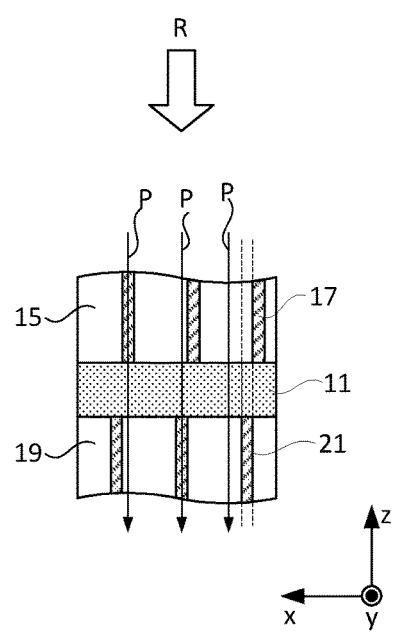

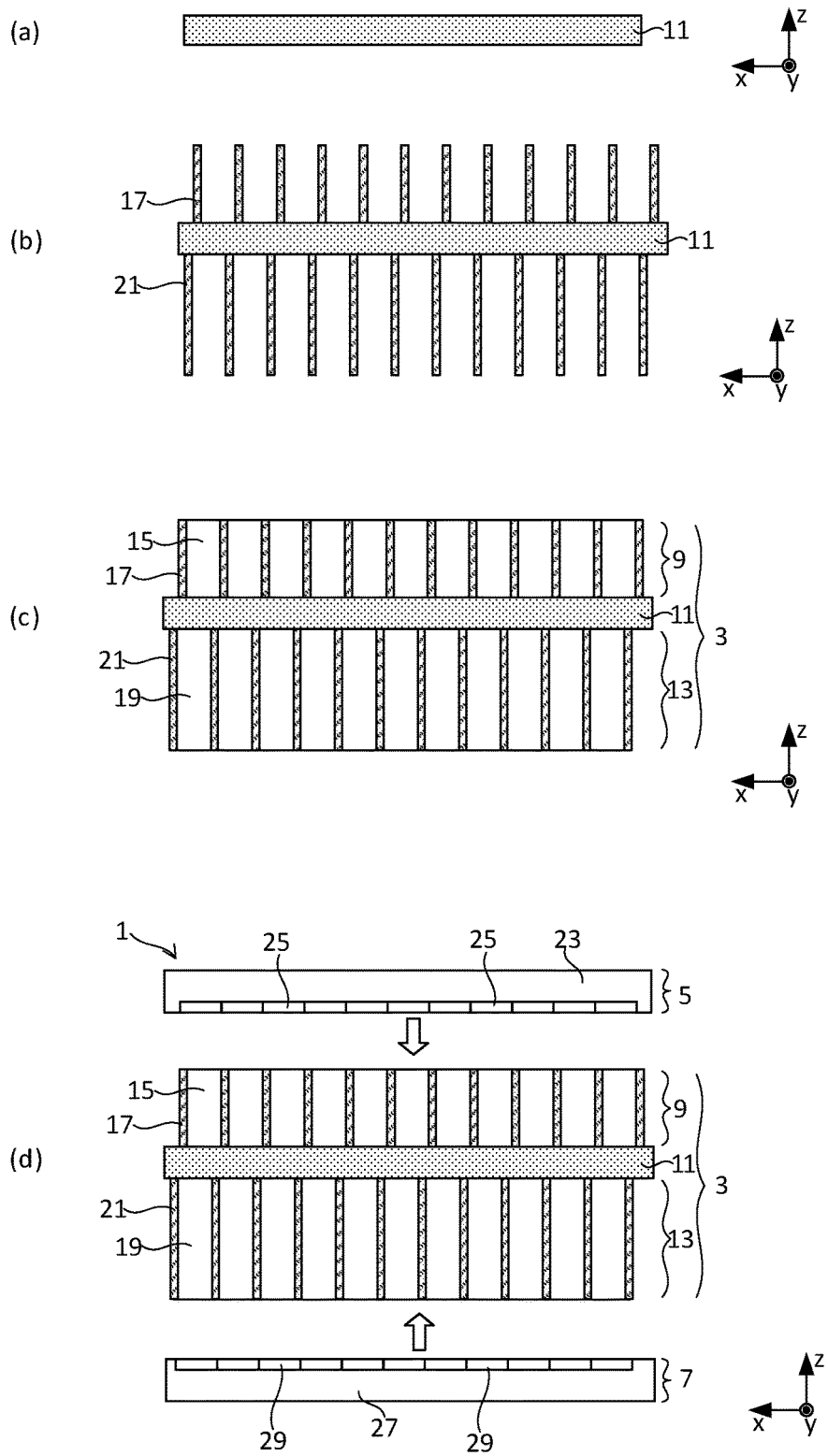
[Fig. 4]

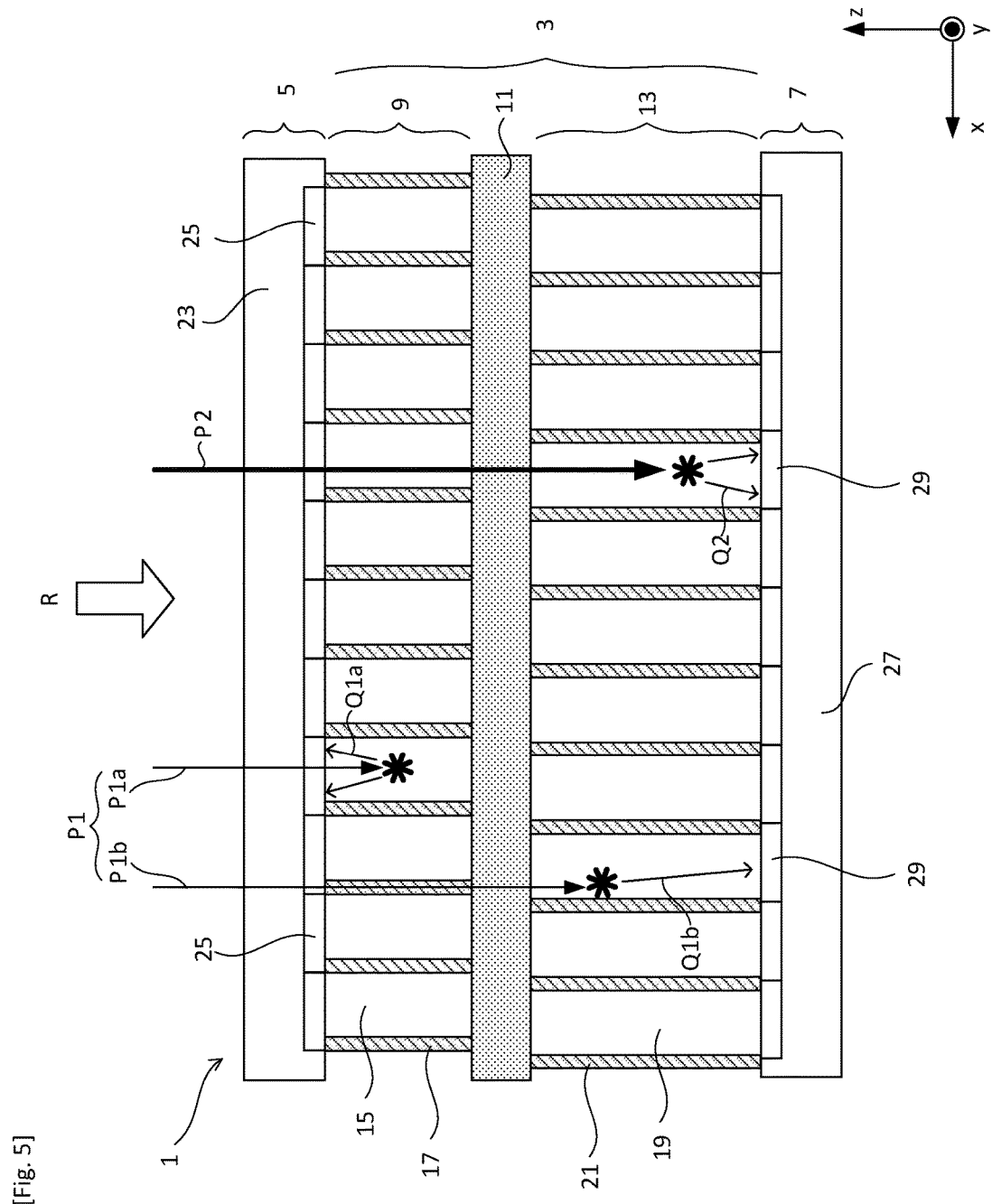
[Fig. 5]

[Fig. 6]
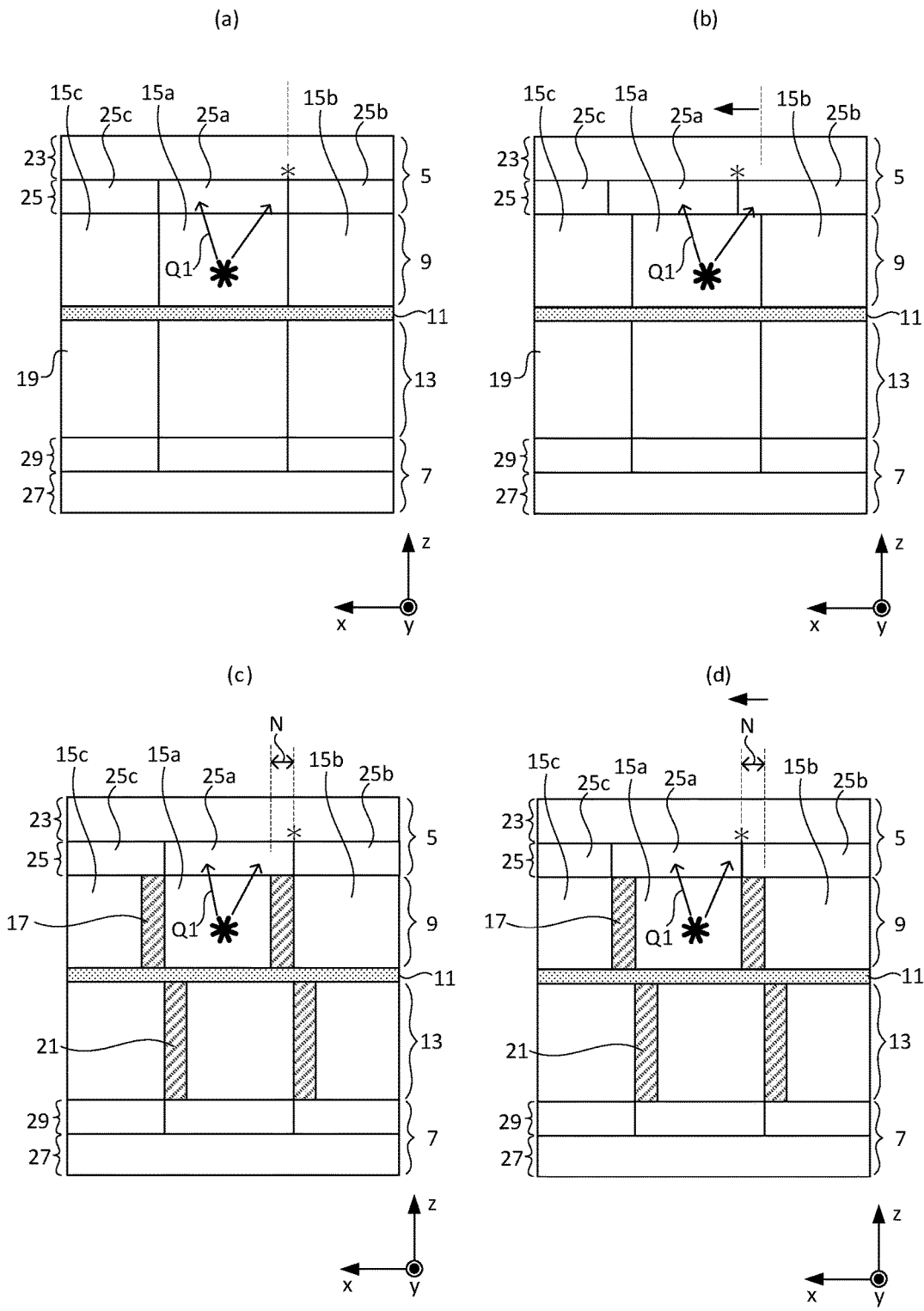

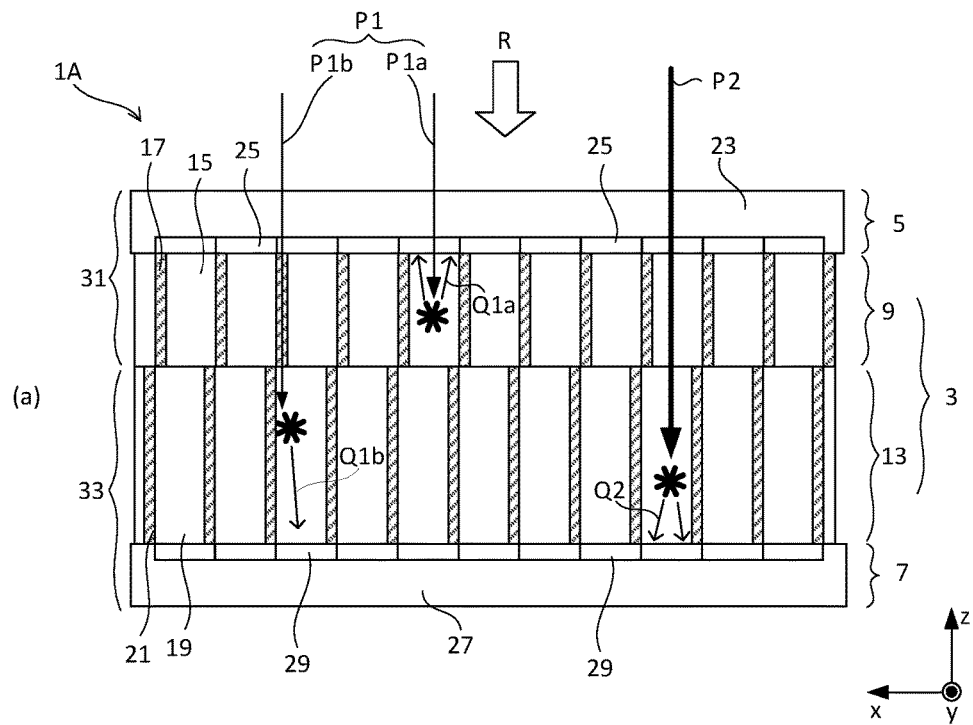
[Fig. 7]

[Fig. 8]
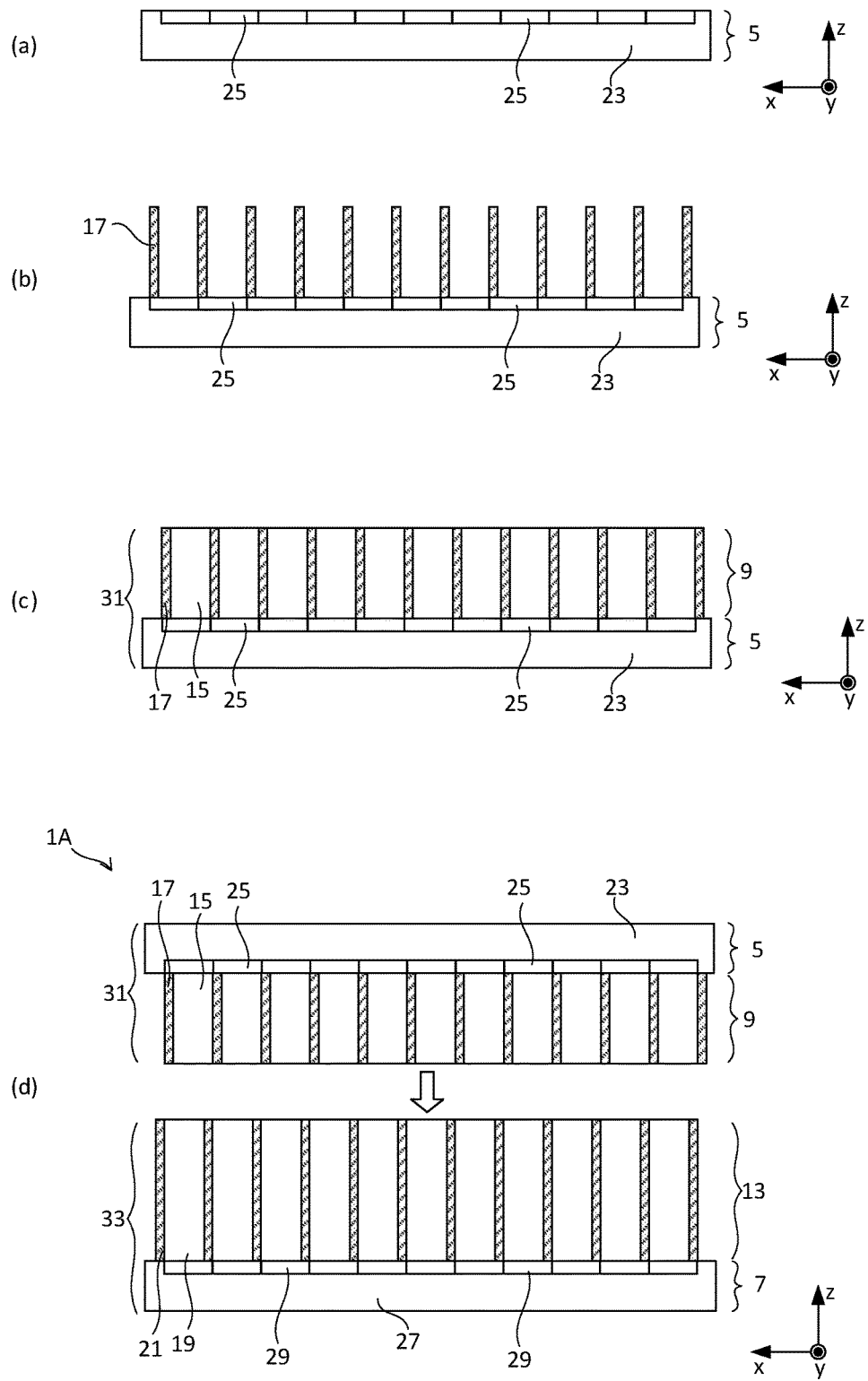

[Fig. 9]
(a)
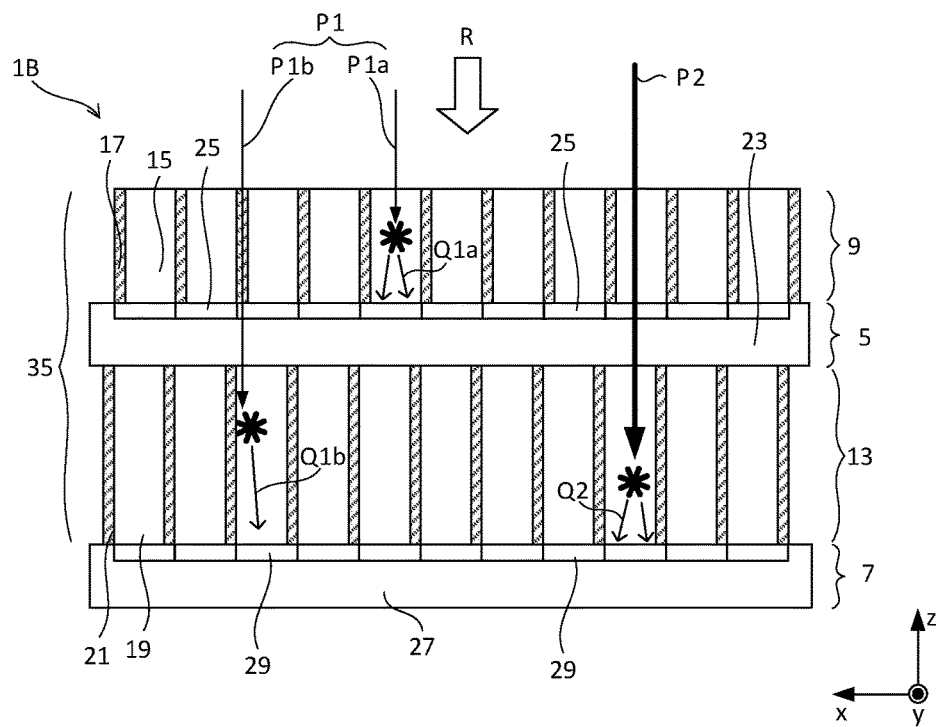
(b)
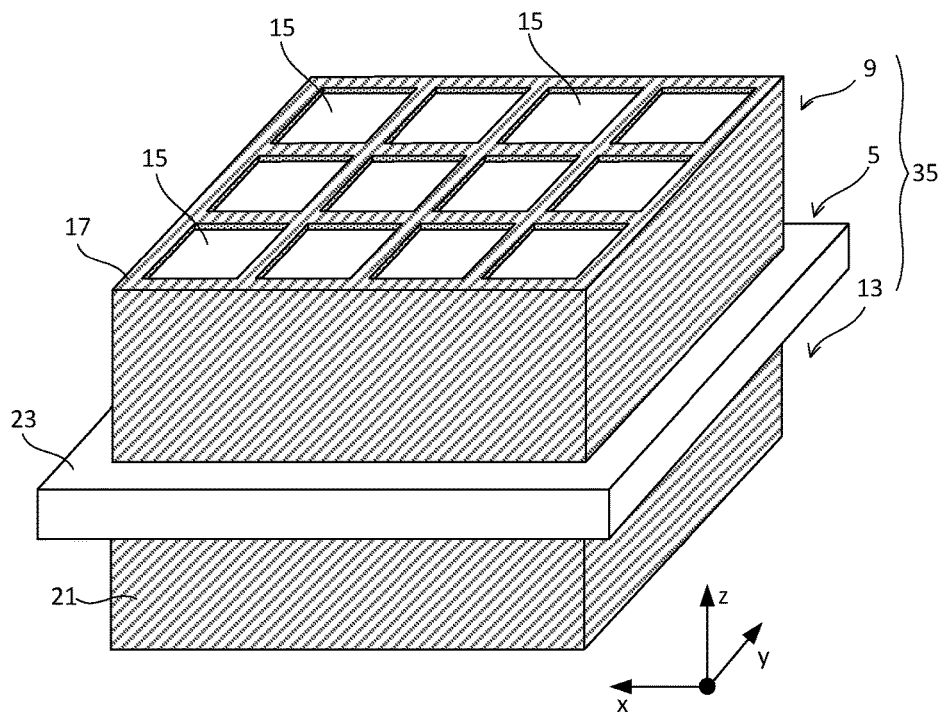

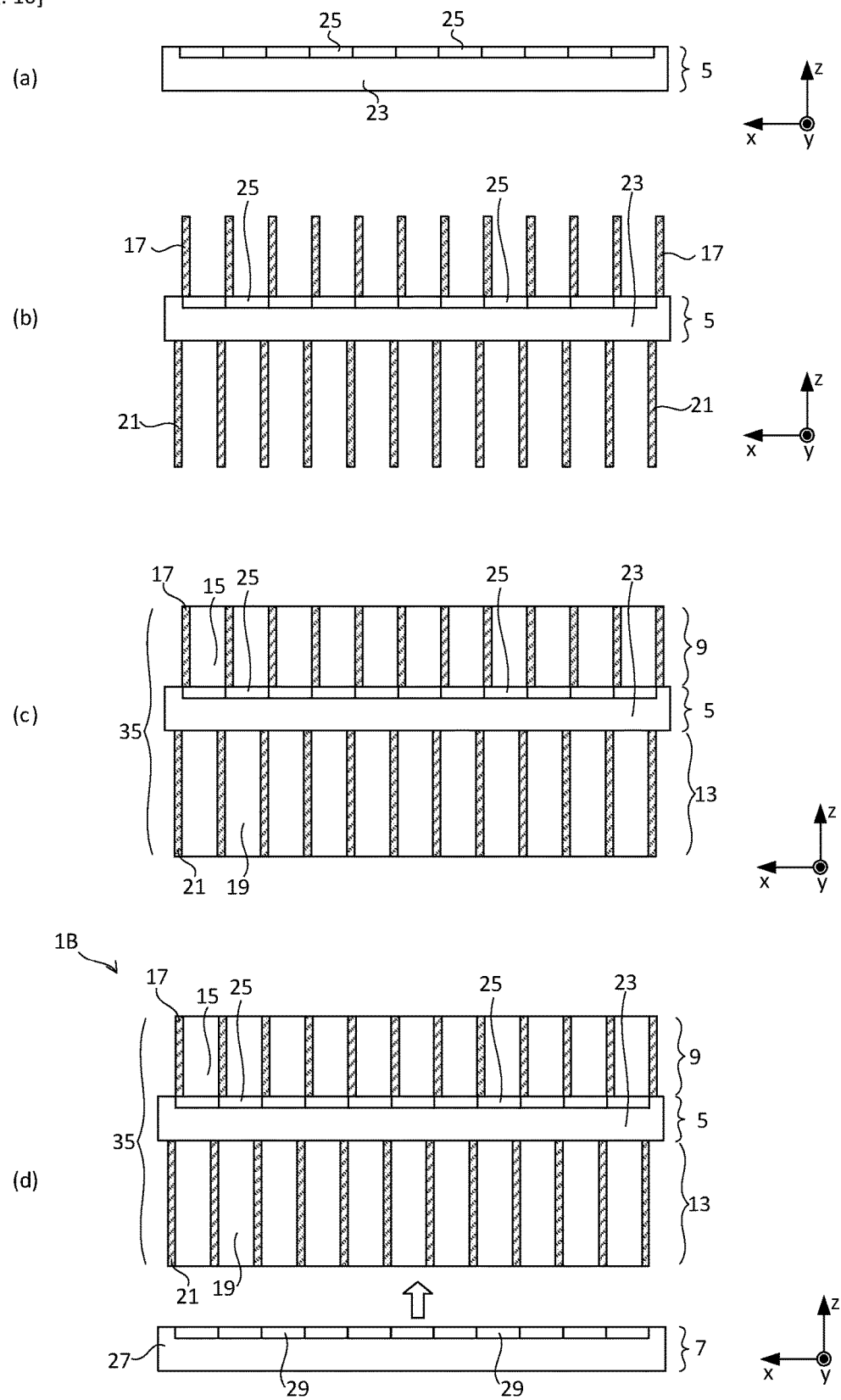
[Fig. 10]

[Fig. 11]
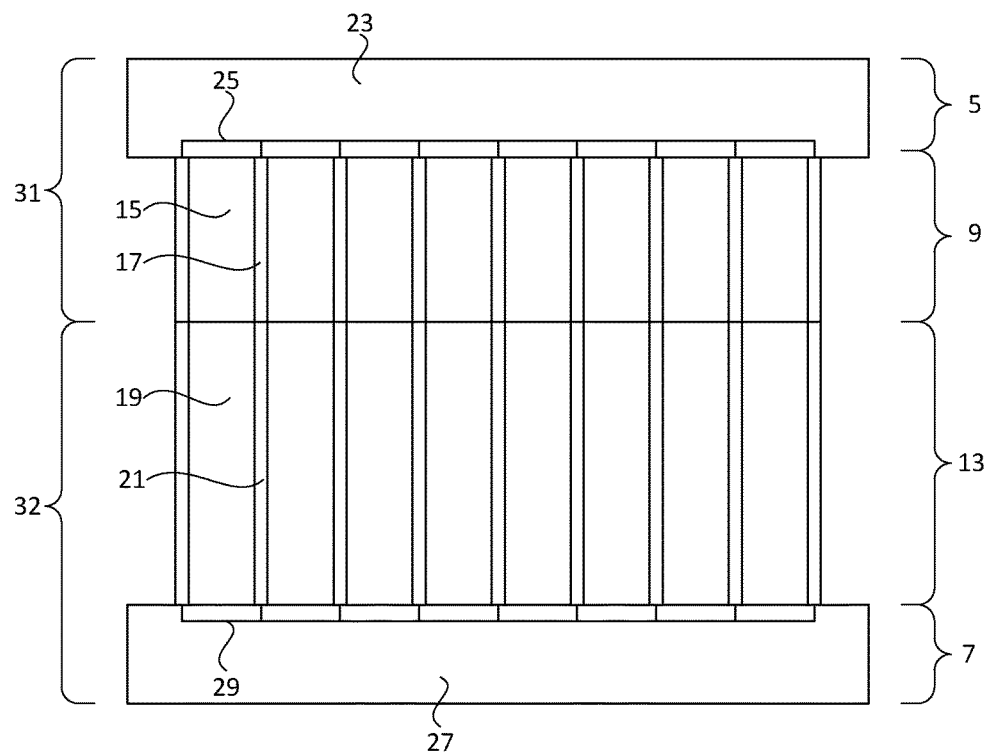
[Fig. 12]
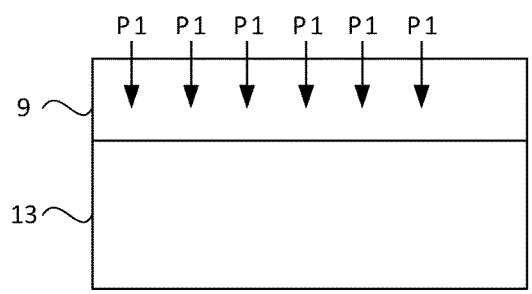
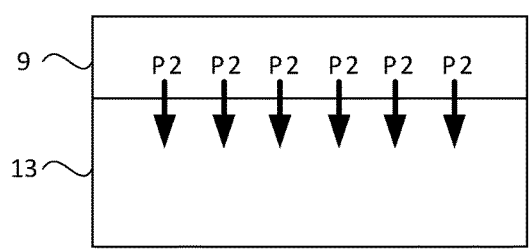

[Fig. 13]
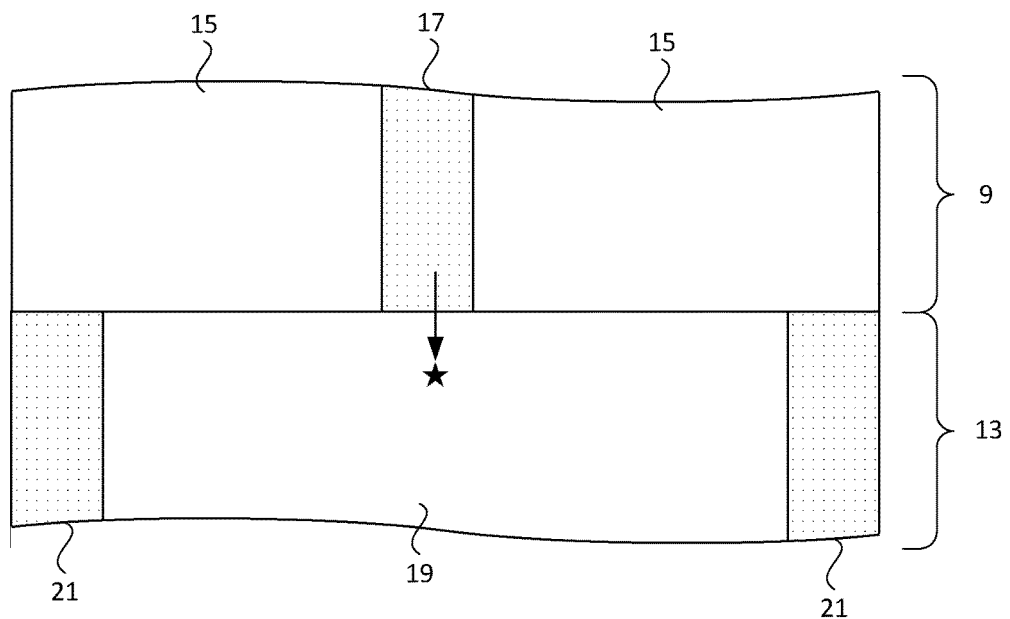
[Fig. 14]
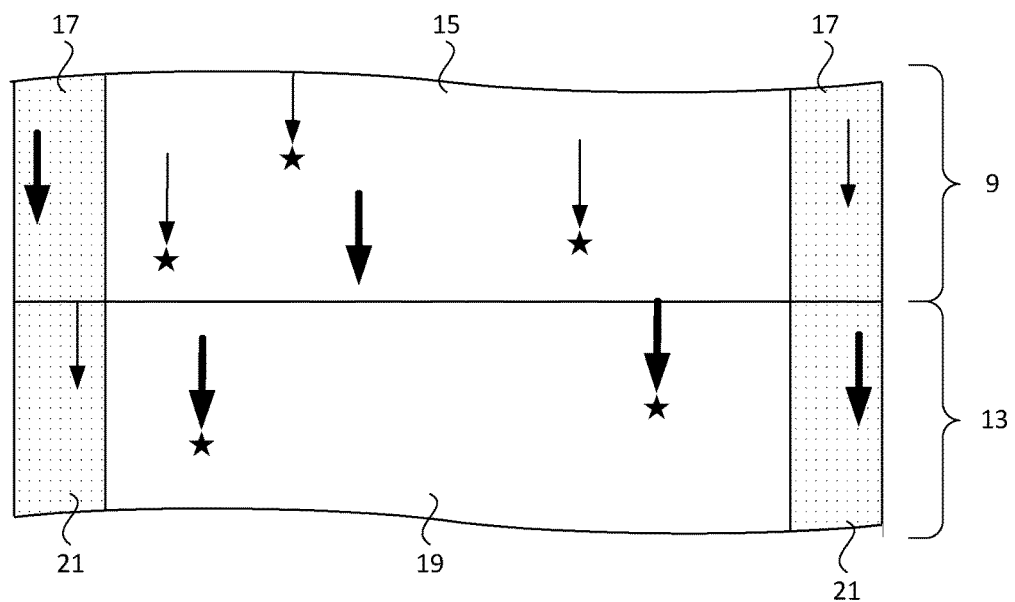

[Fig. 15]
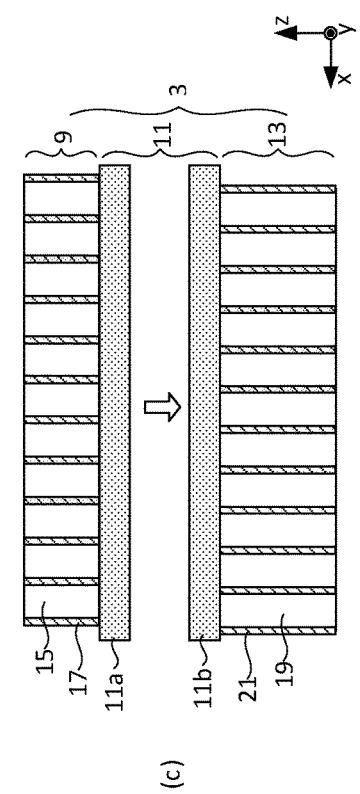
(a)
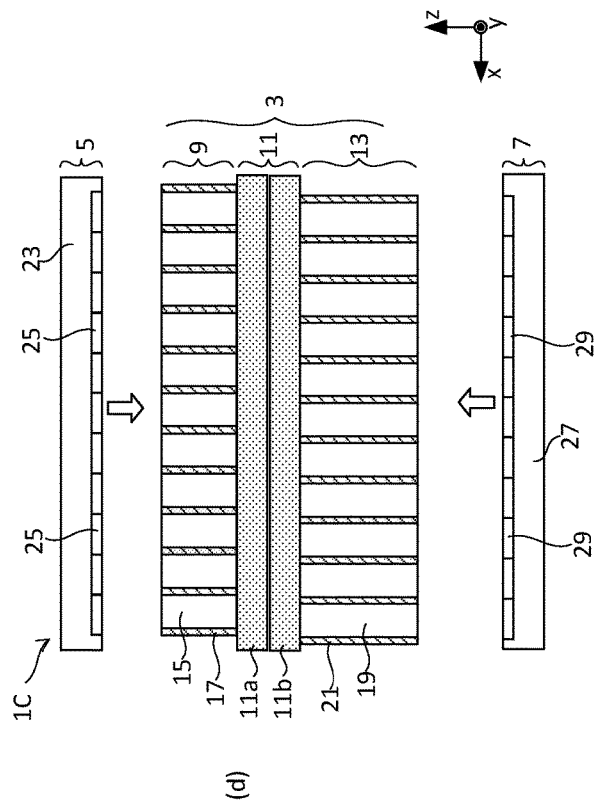
(c)
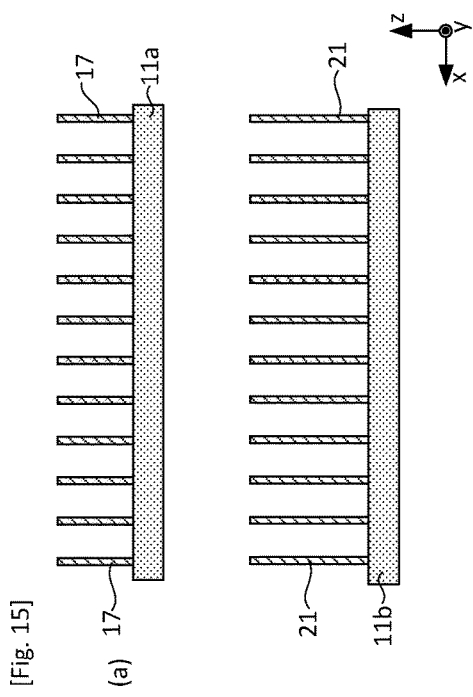
(b)
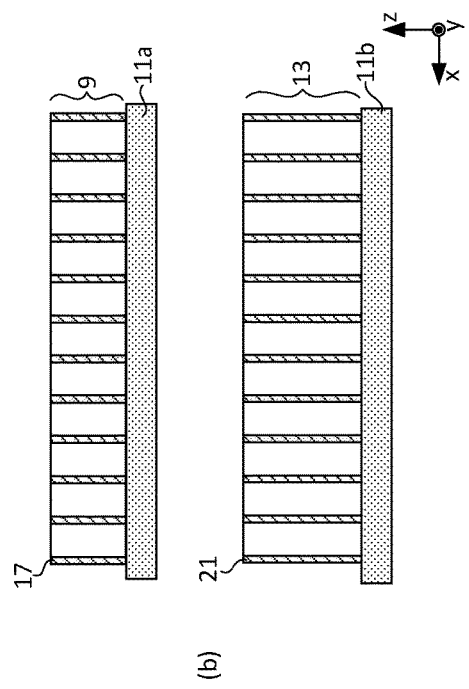
(d)

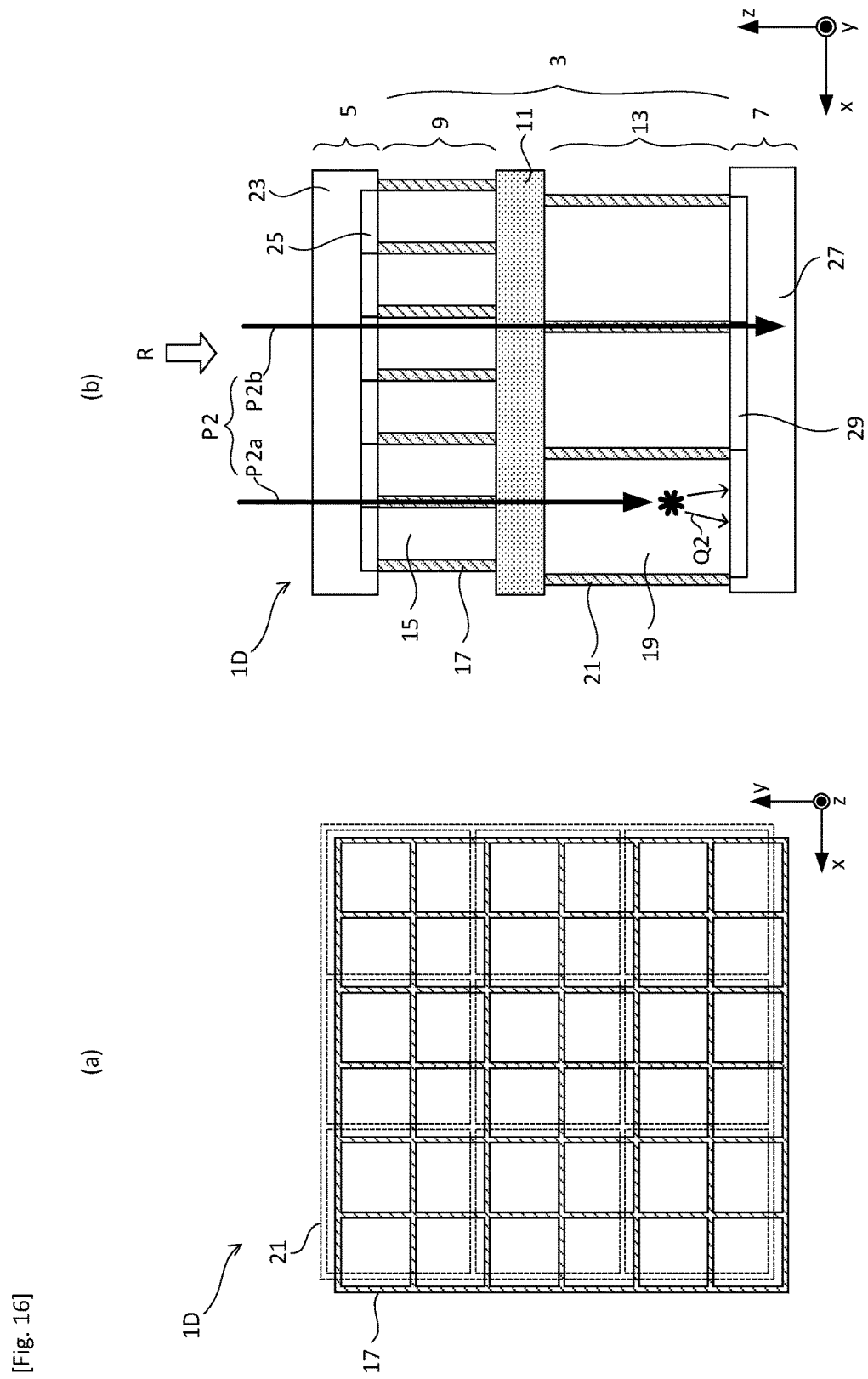

[Fig. 17]
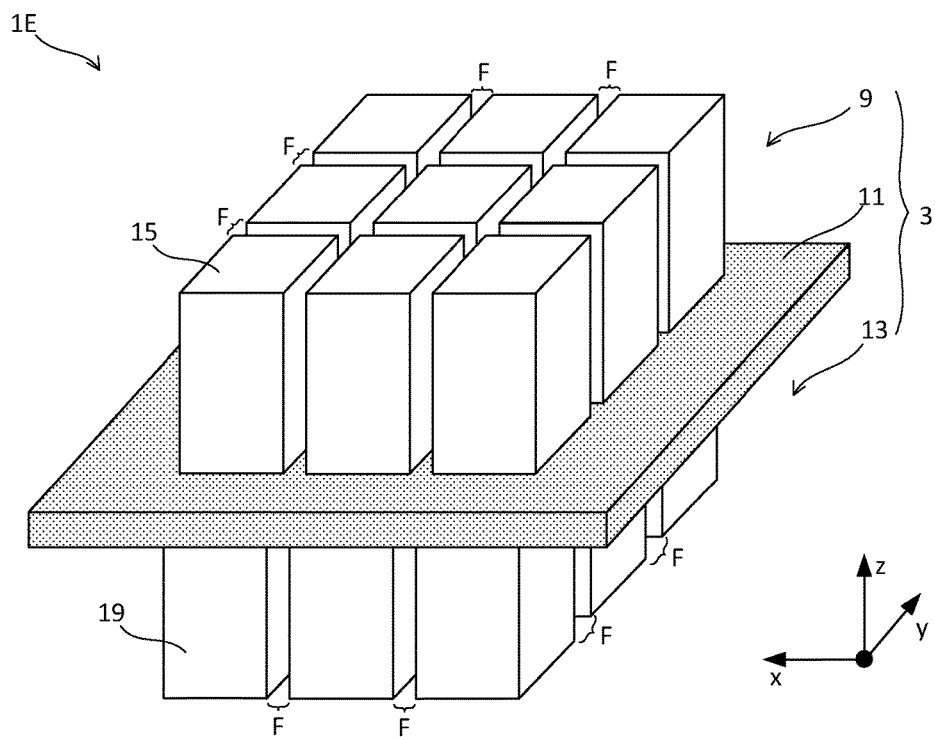
[Fig. 18]
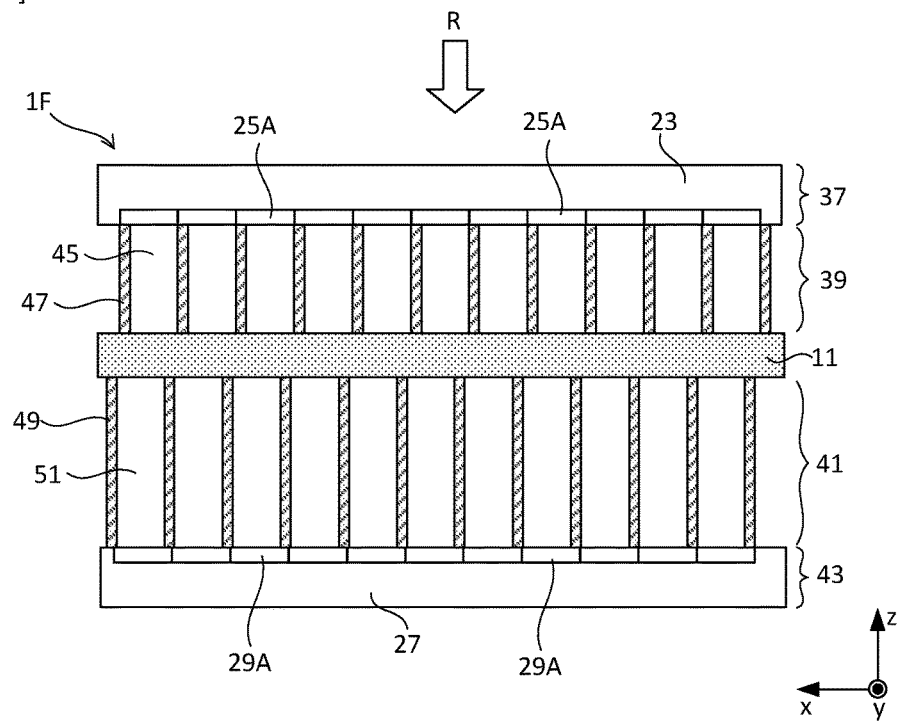

[Fig. 19]
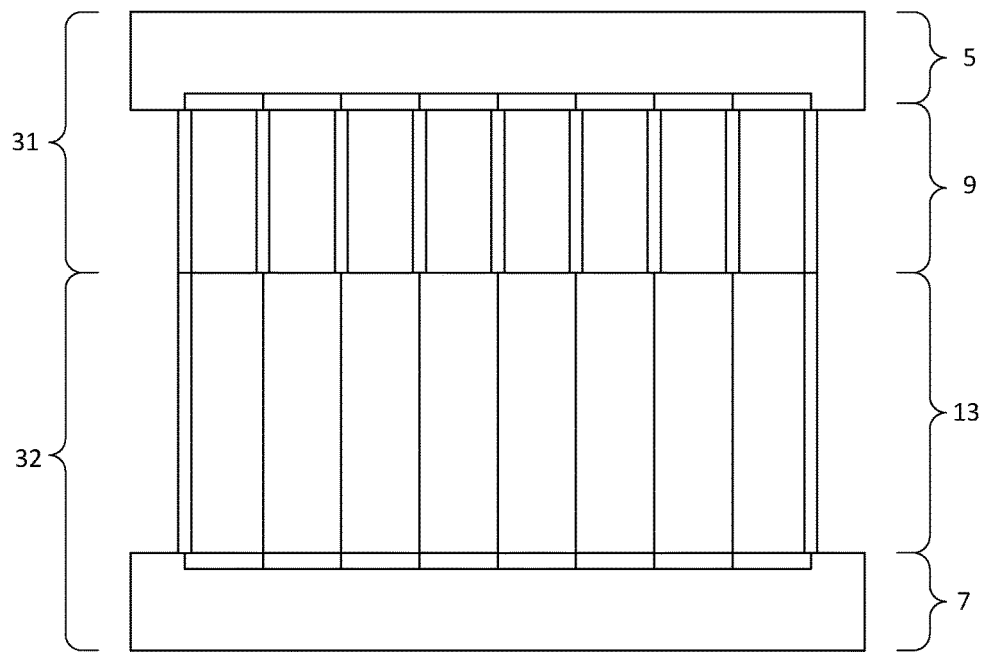
[Fig. 20]
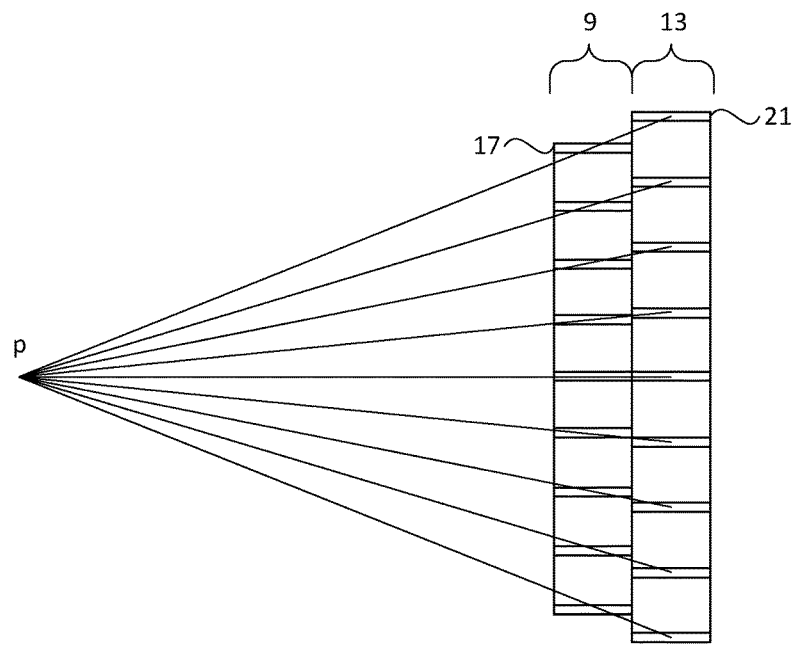

[Fig. 21]
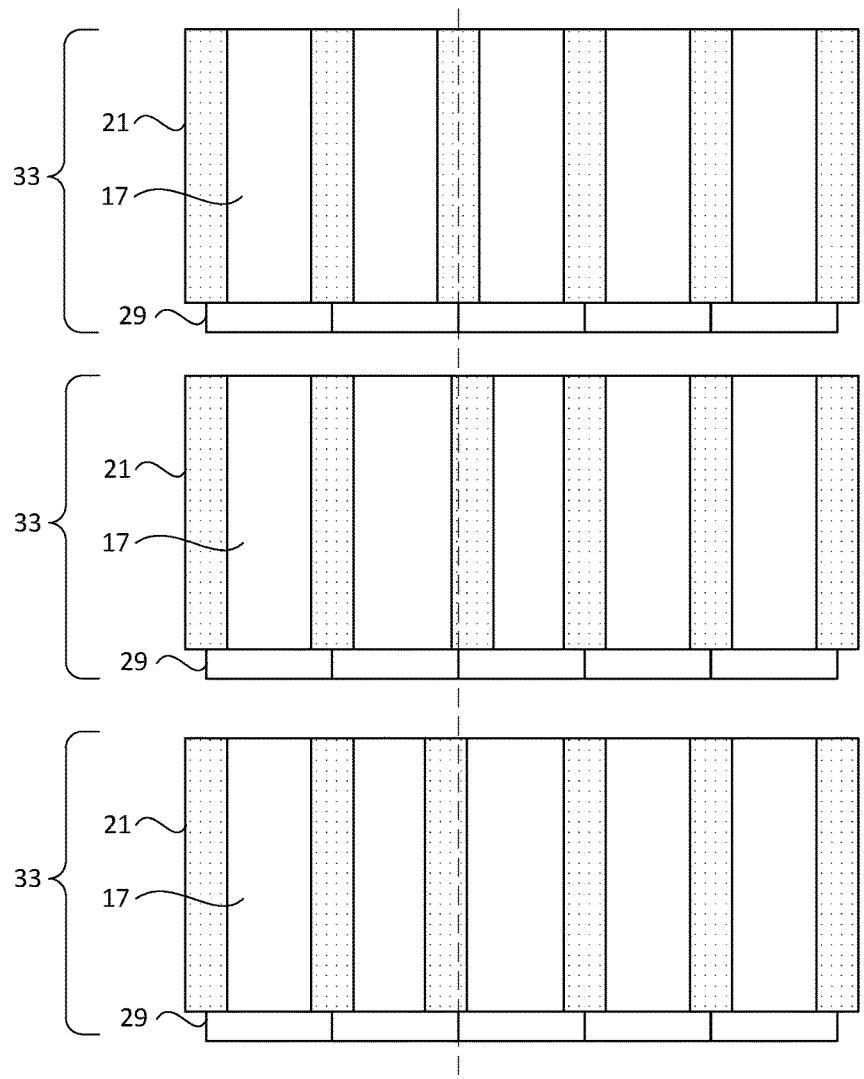
[Fig. 22]
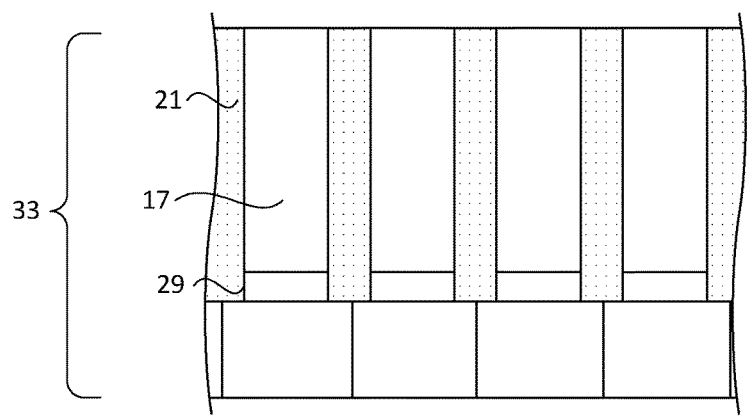

[Fig. 23]
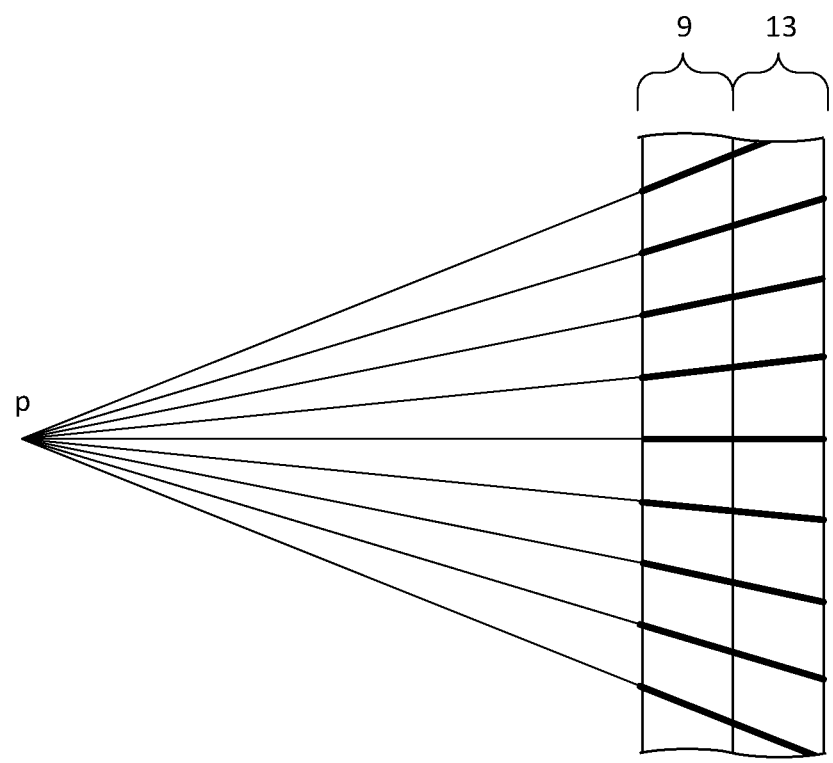

[Fig. 24]
(a) 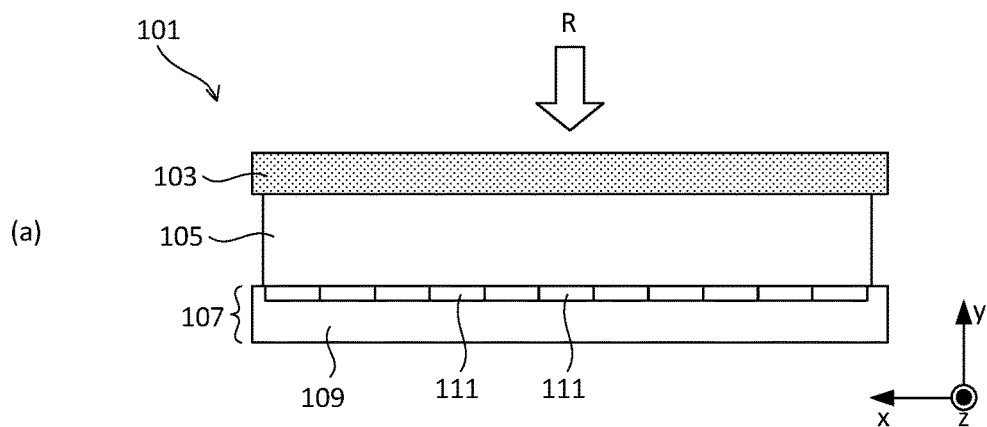
(b) 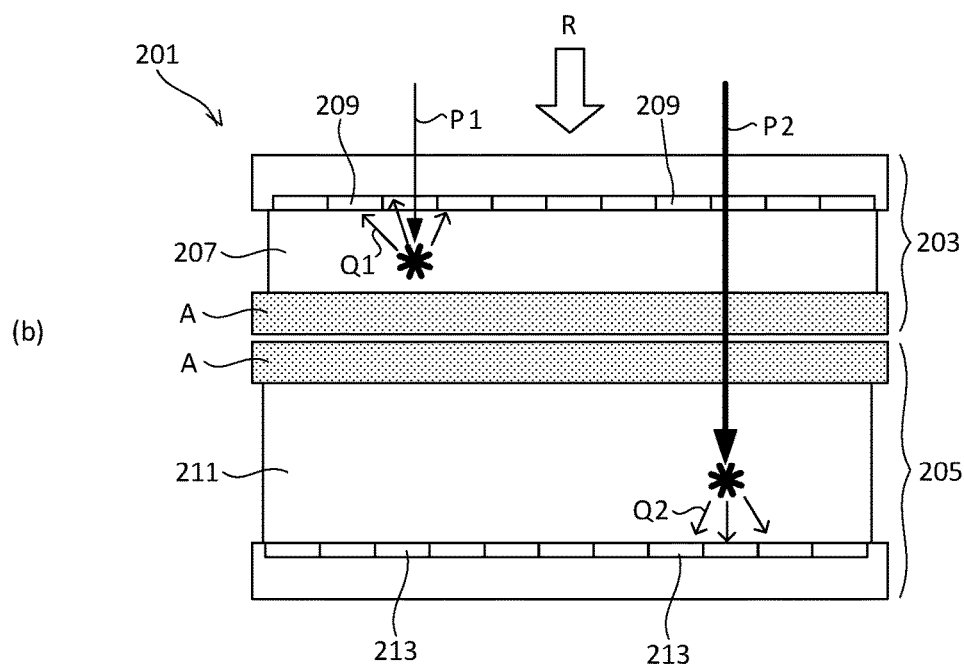

[Fig. 25]
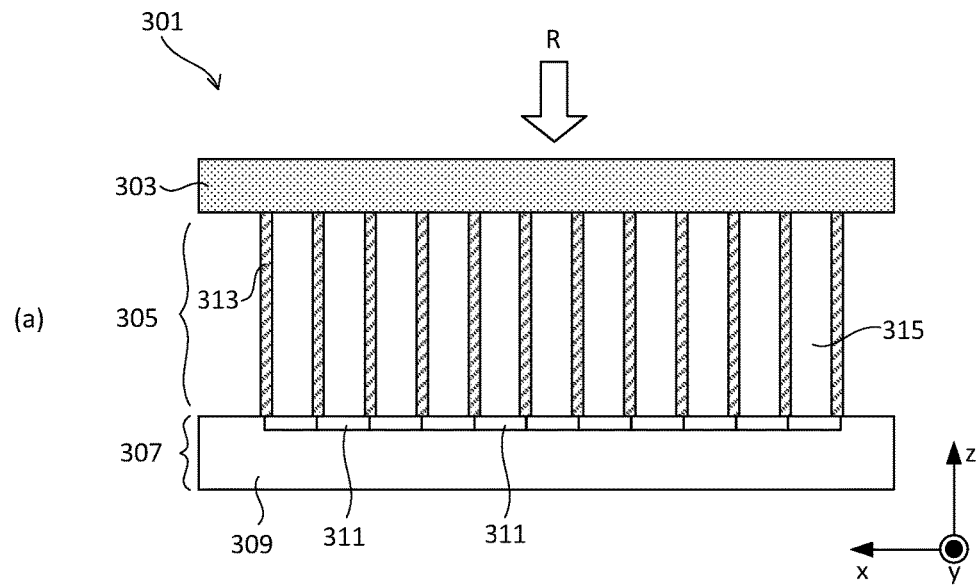
(a)
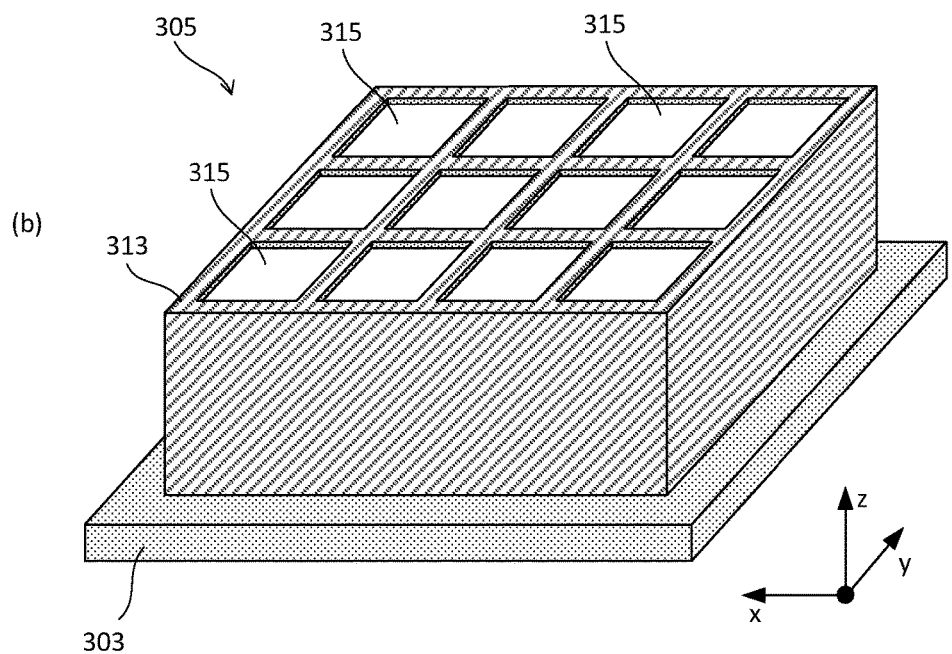
(b)

X-RAY DETECTOR

TECHNICAL FIELD

The present invention relates an X-ray detector employed in a medical diagnosis apparatus or the like, and more particularly, to an X-ray detector applicable to dual energy type X-ray imaging capable of detecting two types of X-rays having different energy ranges.

BACKGROUND ART

In the related art, an X-ray imaging device is employed as a medical X-ray image photographing device. In addition, as an X-ray detector employed in the X-ray imaging device, for example, a flat panel type X-ray detector (hereinafter, abbreviated as an "FPD") is known in the related art.

As illustrated in FIG. 24(a), an FPD 101 of the related art has a stacked structure obtained by stacking a panel-like base material 103, a scintillator panel 105, and a photodetection panel 107 sequentially in this order. The scintillator panel 105 has a scintillator element that absorbs an X-ray and converts it into light. The photodetection panel 107 has a substrate 109 and pixels 111 arranged in a two-dimensional matrix shape. Each of the pixels 111 has a photoelectric conversion element and an output element (not illustrated).

Referring to FIG. 24(a), an X-ray incident to the FPD 101 from a direction indicated by a reference symbol R is converted into light in the scintillator element provided in the scintillator panel 105, and the light is emitted as scintillator light. The scintillator light emitted from the scintillator panel 105 is transmitted to the pixel 111. In addition, the photoelectric conversion element provided in the pixel 111 photoelectrically converts the scintillator light to output an X-ray detection signal as an electric signal from the output element. Furthermore, an X-ray image is created on the basis of the output X-ray detection signal.

In recent years, in the field of medical industry, so-called dual energy imaging is performed to photograph the same part of the inspection target object at different tube voltages. In the dual energy imaging, X-ray images based on X-rays having different energy distributions are created independently, so that differences between elements of the inspection target object can be visualized. For example, by taking a difference between an X-ray image based on the low-energy X-rays and an X-ray image based on the high-energy X-rays, an X-ray image of a hard-tissue such as bones and an X-ray image of a soft tissue such as muscles can be distinguished.

When the photographing in the dual energy imaging is performed by changing the tube voltage, the X-ray irradiation is performed twice. For this reason, diagnostic performance of the X-ray image is degraded due to a body movement of the inspection target object. In this regard, an X-ray detector capable of obtaining a pair of X-ray images including the X-ray image based on low-energy X-rays and the X-ray image based on high-energy X-rays out of the irradiated X-rays by irradiating X-rays onto the inspection target object once has been proposed (for example, see Patent Literature 1). Such an X-ray detector capable of obtaining the X-ray image based on low-energy X-rays and the X-ray image based on high-energy X-rays through a single X-ray irradiation will be referred to hereinafter as a "dual energy type" X-ray detector. In addition, X-ray detectors other than the dual energy type X-ray detector will be distinguished as a "typical" X-ray detector.

Such a dual energy type X-ray detector 201 has a structure in which a pair of FPDs 101 illustrated in FIG. 24(a) are overlapped. That is, as illustrated in FIG. 24(b), a first FPD 203 for detecting relatively low-energy X-rays and a second FPD 205 for detecting relatively high-energy X-rays are stacked in an X-ray irradiation direction indicated by the reference symbol "R." A low-energy X-rays P1 are converted by a scintillator element 207 provided in the FPD 203 into scintillator light Q1 and are converted into electric signals in pixels 209.

Meanwhile, a high-energy X-rays P2 pass through the scintillator element 207 and are converted into scintillator light Q2 in a scintillator element 211 provided in the FPD 205. The scintillator light Q2 is converted into the electric signal in a pixel 213. The FPDs 203 and 205 are stacked while base materials A provided in each FPD face each other. Note that it is necessary to make the thickness of the scintillator element relatively thick in order to absorb and detect high-energy X-rays. That is, compared to the scintillator element 207, the scintillator element 211 typically has a larger thickness.

In this regard, a structure in which the scintillator elements are partitioned by partitioning walls in a typical FPD structure different from the dual energy type X-ray detector has been proposed (for example, see Patent Literature 2). A typical FPD 301 in which the scintillator elements are partitioned by the partitioning walls will now be described with reference to FIGS. 25(a) and 25(b). Similar to the FPD 101 of FIG. 24(a), the FPD 301 has a stacked structure obtained by stacking a base material 303, a scintillator panel 305, and a photodetection panel 307, and the photodetection panel has a substrate 309 and pixels 311 (FIG. 25(a)).

As illustrated in FIG. 25(b), the scintillator panel 305 has grid-like light blocking walls 313 and scintillator elements 315. Each of the scintillator elements 315 is filled in a cell space partitioned by the light blocking wall 313. In general, the pitch of the light blocking wall 313 is set to be substantially equal to (or an integer multiple of) the pitch of the pixel 311.

In this manner, the scintillator panel 305 is shaped such that the scintillator elements 315 arranged in a two-dimensional matrix shape are partitioned by the light blocking walls 313. Since the scattering scintillator light is blocked by the light blocking walls 313, it is possible to prevent the scattering light generated in the scintillator element 315 from reaching a neighboring scintillator element 315. Therefore, by partitioning the scintillator elements 315 using the light blocking walls 313, it is possible to avoid degradation of the resolution of the X-ray image even when the scintillator element 315 is thickened. Such a configuration is useful particularly in the X-ray detector for detecting high-energy X-rays.

In addition, in a structure relating to Patent Literature 2, the pitch of the partitioning wall can be reduced to a short distance such as 60 to 150 μm. For this reason, using the X-ray detector of Patent Literature 2, it is possible to avoid degradation of the resolution of the X-ray image even when an X-ray image having a smaller pixel pitch is required, such as X-ray CT imaging.

CITATION LIST

Patent Literatures

Patent Literature 1: JP-T-2012-26979 (where the term "JP-T" as used herein means a published Japanese translation of a PCT patent application)

Patent Literature 2: International Publication WO 2012/161304

SUMMARY OF THE INVENTION

Problems that the Invention is to Solve

However, such a structure of the related art has the following problems.

Specifically, since the dual energy type X-ray detector of the related art is configured by stacking a pair of typical FPDs, the thickness becomes twice that of the typical FPD. For this reason, in some case, it is difficult to mount the dual energy type FPD onto the X-ray imaging device in which typical FPDs are employed. Therefore, versatility or compatibility of the dual energy type FPD is degraded. In addition, when the scintillator element is thickened, the scintillator light is scattered to the neighboring scintillator elements. Therefore, the resolution of the X-ray image is degraded.

Furthermore, when the dual energy type FPD is manufactured by stacking a pair of typical FPDs, the pixels and the scintillator elements provided in each of the typical FPDs may be misaligned from each other in some cases. In this case, image positions are different between the X-ray image based on low-energy X-rays and the X-ray image based on high-energy X-rays. Therefore, the diagnostic performance of the X-ray image created from the dual energy imaging is seriously degraded.

In view of the aforementioned problems, an object of the invention is to provide a higher sensitivity X-ray detector capable of performing dual energy imaging with high diagnostic performance.

Means for Solving the Problems

In order to achieve such objects, the invention provides the following features.

Specifically, according to the invention, there is provided an X-ray detector including: a first scintillator panel provided with a first grid-like light blocking portion and a first scintillator element filled in each cell partitioned by the first light blocking portion in a two-dimensional matrix shape to convert low-energy X-rays out of incident X-rays into light; a second scintillator panel provided with a second grid-like light blocking portion and a second scintillator element filled in each cell partitioned by the second light blocking portion in a two-dimensional matrix shape to convert high-energy X-rays having higher energy than that of the low-energy X-rays out of the incident X-rays into light; a first photodetection panel provided with photoelectric conversion elements arranged in a two-dimensional matrix shape to covert the light converted by the first scintillator element into electric charges; and a second photodetection panel provided with photoelectric conversion elements arranged in a two-dimensional matrix shape to convert the light converted by the second scintillator element into electric charges, in which each of the first and second scintillator panels and the first and second photodetection panels is stacked in an X-ray incidence direction.

[Functional Effect]

Since the first and second scintillator elements are partitioned by the light blocking walls, it is possible to more appropriately avoid occurrence of a trouble in the X-ray detector caused by a positional deviation of the photodetection panel.

Preferably, a grid pattern of the first light blocking portion and a grid pattern of the second light blocking portion deviate from each other along the X-ray incidence face.

[Functional Effect]

It is possible to more appropriately avoid the X-rays incident to the X-ray detector from transmitting through both the first and second light blocking portions. That is, the X-ray is more reliably incident to at least one of the first and second scintillator elements and is converted into light.

In the invention described above, a pitch of the second light blocking portion is preferably larger than a pitch of the first light blocking portion.

[Functional Effect]

That is, the number of the second light blocking portions is smaller than the number of the first light blocking portions. By reducing an area where the second light blocking portions are formed, an area where both low-energy X-rays and high-energy X-rays can be detected in the X-ray detector is widened. As a result, it is possible to further improve X-ray sensitivity of the X-ray detector.

In the X-ray detector described above, it is preferable that a ratio between the pitch of the first light blocking portion and the pitch of the second light blocking portion be equal to a ratio between a spreading width obtained when radiation beams spreading radially from a radiation source reach the first light blocking portion and a spreading width obtained when the radiation beams reach the second light blocking portion.

[Functional Effect]

In the aforementioned configuration, it is possible to provide an X-ray detector having high sensitivity by preventing X-rays spreading radially from being incident to the light blocking portion as many as possible.

In the invention described above, preferably, the X-ray detector further has a planar substrate, the first scintillator panel is formed on one surface of the substrate, and the second scintillator panel is formed on the other surface of the substrate.

[Functional Effect]

Since the first and second scintillator panels are formed integrally with the substrate, it is possible to more appropriately avoid misalignment of the scintillator panels. Therefore, the grid patterns of the first and second light blocking portions can be more reliably formed to deviate along the X-ray incidence face.

In the invention described above, it is preferable that the first photodetection panel, the first scintillator panel, the second scintillator panel, and the second photodetection panel be stacked sequentially in this order, and the first scintillator panel and the second scintillator panel be directly stacked.

[Functional Effect]

Since the first and second scintillator panels are directly stacked, it is possible to reduce the thickness of the dual energy type X-ray detector as a whole. Therefore, it is possible to improve resolution of the X-ray image and improve compatibility and versatility.

In the invention described above, it is preferable that the first scintillator panel, the first photodetection panel, the second scintillator panel, and the second photodetection panel be stacked sequentially in this order.

[Functional Effect]

The X-rays are first incident to the first scintillator panel and is then incident to the first photodetection panel. That is, since it is possible to avoid the X-rays from being directly incident to the first photodetection panel, it is possible to appropriately avoid deterioration of the first photodetection panel caused by X-rays.

Preferably, a grid pattern of the first light blocking portion and a grid pattern of the second light blocking portion are aligned with each other, so that the scintillator element of the second scintillator panel is linked to the scintillator element of the first scintillator panel.

[Functional Effect]

Using the aforementioned configuration, it is possible to provide an X-ray detector having a high energy resolution. Since the grid pattern of the light blocking wall of the first light blocking portion is aligned with the grid pattern of the light blocking wall of the second light blocking portion, a low-energy X-ray passing through the first light blocking portion of the first scintillator panel is incident to the first light blocking portion of the second scintillator panel and directly passes through the second scintillator panel. This X-ray is not detected by the X-ray detector. The second photodetection panel ideally operates to detect only a high-energy X-ray.

In the X-ray detector described above, a pitch of the light blocking portion is preferably different depending on a position of the light blocking portion.

[Functional Effect]

In this configuration, it is possible to more freely change the configuration of the X-ray detector. For example, it is possible to provide a configuration optimal to imaging using an X-ray source emitting X-rays spreading radially.

In the X-ray detector described above, the photoelectric conversion element is preferably placed inside a partition formed by the grid of the light blocking portion.

[Functional Effect]

In this configuration, it is possible to reliably optically partition the neighboring photoelectric conversion elements.

In the X-ray detector described above, the light blocking wall included in the grid of the light blocking portion is preferably gradually inclined from a center of the grid to an end portion.

[Functional Effect]

In this configuration, it is possible to provide an X-ray detector having high sensitivity by preventing X-rays spreading radially from being incident to the light blocking portion as many as possible.

According to another aspect of the invention, there is provided an X-ray detector including: a first scintillator panel provided with first scintillator elements that convert low-energy X-rays out of incident X-rays into light; a second scintillator panel provided with a second grid-like light blocking portion and second scintillator elements filled in each cell partitioned by the second light blocking portion in a two-dimensional matrix shape to convert high-energy X-rays having higher energy than that of the low-energy X-rays out of the incident X-rays into light; a first photodetection panel provided with photoelectric conversion elements arranged in a two-dimensional matrix shape to covert the light converted by the first scintillator elements into electric charges; and a second photodetection panel provided with photoelectric conversion elements arranged in a two-dimensional matrix shape to convert the light converted by the second scintillator elements into electric charges, in which each of the first scintillator panel, the second scintillator panel, the first photodetection panel, and the second photodetection panel is stacked in an incidence direction of the X-ray.

[Functional Effect]

In this configuration, it is possible to simplify an apparatus configuration and provide an X-ray detector with a lower cost.

Advantage of the Invention

Since the X-ray detector according to the invention is configured such that the grid pattern of the first light blocking portion of the first scintillator panel deviates from the grid pattern of the second light blocking portion of the second scintillator panel along the X-ray incidence face, it is possible to more appropriately prevent the X-rays incident to the X-ray detector from passing through both the first and second light blocking portions. That is, the X-ray is more reliably incident to at least one of the first and second scintillator elements and is converted into light.

Low-energy X-rays out of the X-rays are converted into light in the first scintillator elements, and the light is converted into electric charges in the first photodetection panel. In addition, high-energy X-rays having higher energy than that of the low-energy X-rays are converted into light in the second scintillator element, and the light is converted into electric charges in the second photodetection panel. For this reason, out of the X-rays, at least one of the low-energy X-rays and the high-energy X-rays is converted into an electric charge and is detected. Therefore, since it is possible to remarkably reduce an area where it is difficult to detect an X-ray in the X-ray detector, it is possible to remarkably improve X-ray sensitivity of the X-ray detector.

BRIEF DESCRIPTION OF THE DRAWINGS

FIGS. 1(a) and 1(b) are schematic diagrams illustrating a whole configuration of an X-ray detector according to a first embodiment, in which FIG. 1(a) is a cross-sectional view illustrating the X-ray detector, and FIG. 1(b) is a bird's-eye view illustrating a schematic configuration of a scintillator block according to the first embodiment.

FIG. 2 is a plan view illustrating a positional relationship of each light blocking wall in the X-ray detector according to the first embodiment.

FIG. 3 is a cross-sectional view illustrating a position relationship of the light blocking wall according to the first embodiment.

FIGS. 4(a) to 4(d) are diagrams illustrating a preferable manufacturing process for the X-ray detector according to the first embodiment.

FIG. 5 is a cross-sectional view illustrating a configuration for detecting X-rays in the X-ray detector according to the first embodiment.

FIGS. 6(a) to 6(d) are cross-sectional views illustrating an allowable range regarding a positional deviation of a photodetection panel in the X-ray detector according to the first embodiment, in which FIG. 6(a) is a cross-sectional view illustrating an ideal position of the photodetection panel in a configuration having no light blocking wall, and FIG. 6(b) is a cross-sectional view illustrating a state in which a positional deviation of the photodetection panel is generated in the configuration having no light blocking wall, FIG. 6(c) is a cross-sectional view illustrating an ideal position of the photodetection panel in a configuration having the light blocking wall, and FIG. 6(d) is a cross-sectional view illustrating a state in which a positional deviation of the photodetection panel is generated in the configuration having the light blocking wall.

FIGS. 7(a) and 7(b) are schematic diagrams illustrating a whole configuration of an X-ray detector according to a second embodiment, in which FIG. 7(a) is a cross-sectional view illustrating a whole configuration of the X-ray detector according to the second embodiment, and FIG. 7(b) is a bird's-eye view illustrating a schematic configuration of the detection panel according to the second embodiment.

FIGS. 8(a) to 8(d) are diagrams illustrating a preferable manufacturing process for the X-ray detector according to the second embodiment.

FIGS. 9(a) and 9(b) are schematic diagrams illustrating a whole configuration of an X-ray detector according to a third embodiment, in which FIG. 9(a) is a cross-sectional view illustrating a whole configuration of the X-ray detector according to the third embodiment, and FIG. 9(b) is a bird's-eye view illustrating a schematic configuration of a scintillator assembly according to the third embodiment.

FIGS. 10(a) to 10(d) are diagrams illustrating a preferable manufacturing process for the X-ray detector according to the third embodiment.

FIG. 11 is a schematic diagram illustrating an X-ray detector according to a fourth embodiment.

FIG. 12 is a schematic diagram illustrating an effect of the X-ray detector according to the fourth embodiment.

FIG. 13 is a schematic diagram illustrating an effect of the X-ray detector according to the fourth embodiment.

FIG. 14 is a schematic diagram illustrating an effect of the X-ray detector according to the fourth embodiment.

FIGS. 15(a) to 15(d) are diagrams illustrating a preferable manufacturing process for the X-ray detector in a modification (1).

FIGS. 16(a) and 16(b) are diagrams illustrating a configuration of an X-ray detector in a modification (4), in which FIG. 16(a) is a plan view illustrating a pitch and a position relationship of each light blocking wall, and FIG. 16(b) is a cross-sectional view illustrating the X-ray detector.

FIG. 17 is a bird's-eye view illustrating a configuration of a scintillator block in a modification (5).

FIG. 18 is a cross-sectional view illustrating a configuration of an X-ray detector in a modification (6).

FIG. 19 is a cross-sectional view illustrating a configuration of an X-ray detector in a modification of the invention.

FIG. 20 is a cross-sectional view illustrating a configuration of the X-ray detector in a modification of the invention.

FIG. 21 is a cross-sectional view illustrating a configuration of the X-ray detector in a modification of the invention.

FIG. 22 is a cross-sectional view illustrating a configuration of the X-ray detector in a modification of the invention.

FIG. 23 is a cross-sectional view illustrating a configuration of the X-ray detector in a modification of the invention.

FIGS. 24(a) and 24(b) are cross-sectional views illustrating a whole configuration of the X-ray detector in the related art, in which FIG. 24(a) is a cross-sectional view illustrating a configuration of a typical X-ray detector in the related art, and FIG. 24(b) is a cross-sectional view illustrating a configuration of a dual energy type X-ray detector in the related art.

FIGS. 25(a) and 25(b) are schematic diagrams illustrating a whole configuration of the typical X-ray detector provided with the light blocking wall in the related art, in which FIG. 25(a) is a cross-sectional view illustrating a configuration of the typical X-ray detector provided with the light blocking wall, and FIG. 25(b) is a bird's-eye view illustrating a position relationship between the scintillator element and the light blocking wall.

MODE FOR CARRYING OUT THE INVENTION

First Embodiment

A first embodiment of the invention will now be described with reference to the accompanying drawings.

FIG. 1 is a cross-sectional view illustrating a whole configuration of the X-ray detector according to the first embodiment. In addition, as the X-ray detector according to the first embodiment, a flat panel type detector (FPD) will be described by way of example.

<Description of Whole Configuration>

As illustrated in FIG. 1, an X-ray detector 1 according to the first embodiment has a scintillator block 3, a photodetection panel 5, and a photodetection panel 7. The scintillator block 3 has a panel-like structure widened in a two-dimensional direction. The photodetection panel 5 is provided on one surface of the scintillator block 3, and the photodetection panel 7 is provided on the other surface of the scintillator block 3. That is, the X-ray detector 1 has a stacked structure obtained by stacking the photodetection panel 5, the scintillator block 3, and the photodetection panel 7 sequentially in this order.

As illustrated in FIG. 1(b), the scintillator block 3 has a stacked structure obtained by stacking a scintillator panel 9, a substrate 11, and a scintillator panel 13 sequentially in this order. The scintillator panel 9 is provided on one surface of the substrate 11 and is shaped such that scintillator elements 15 arranged in a two-dimensional matrix shape are partitioned by grid-like light blocking walls 17. The scintillator panel 13 is provided on the other surface of the substrate 11 and is shaped such that scintillator elements 19 arranged in a two-dimensional matrix shape are partitioned by grid-like light blocking walls 21. The light blocking wall 17 corresponds to a first light blocking portion according to the invention, and the light blocking wall 21 corresponds to a second light blocking portion according to the invention.

That is, in the X-ray detector 1, the scintillator block 3 has an integral structure including the substrate 11, the scintillator panel 9, and the scintillator panel 13. In addition, the scintillator element 19 is preferably thicker than the scintillator element 15 in a z-direction. As a material of the light blocking walls 17 and 21, for example, glass powder containing alkali metal oxide is employed. The scintillator elements 15 and 19 absorb the irradiated X-rays and emit light such as fluorescent light as the scintillator light depending on the irradiated X-rays. As a material of the scintillator elements 15 and 19, an X-ray fluorescent body such as cesium iodide may be employed. In addition, other material known in the art may also be employed as appropriate.

A light reflection film capable of reflecting the scintillator light is preferably provided between the substrate 11 and the scintillator panel 9 and between the substrate 11 and the scintillator panel 13. As a material of the light reflection film, a light reflecting material well known in the art such as thin film aluminum may be appropriately employed. Furthermore, the entire outer circumferences of the scintillator panels 9 and 13 are preferably covered by the light reflection film capable of reflecting the scintillator light.

The photodetection panel 5 includes a substrate 23 and pixels 25 arranged in a two-dimensional matrix shape. Each pixel 25 has a photoelectric conversion element that converts light into electric charges and an output element that outputs X-ray detection signals on the basis of the converted electric charges. Each pixel 25 converts the scintillator light emitted from the scintillator element 15 into an X-ray detection signal and outputs the X-ray detection signal. As illustrated in FIG. 1(a), the pitch of the pixel 25 is preferably substantially equal to the pitch of the light blocking wall 17.

The scintillator element 15 absorbs an X-ray having relatively low energy and converts it into the scintillator light. For this reason, an X-ray image based on low-energy X-rays is created by applying various image processings to the X-ray detection signal output from the photodetection panel 5. The photodetection panel 5 corresponds to a first photodetection panel according to the invention. The scintillator element 15 corresponds to a first scintillator element according to the invention. The scintillator panel 9 corresponds to a first scintillator panel according to the invention.

The photodetection panel 7 includes a substrate 27 and pixels 29 arranged in a two-dimensional matrix shape. Each pixel 29 has a photoelectric conversion element and an output element to convert the scintillator light emitted from the scintillator element 19 into the X-ray detection signal and output the X-ray detection signal. The pitch of the pixel 29 is preferably substantially equal to the pitch of the light blocking wall 21. The photodetection panel 7 corresponds to a second photodetection panel according to the invention. The scintillator panel 13 corresponds to a second scintillator panel according to the invention.

The scintillator element 19 absorbs an X-ray having relatively high energy and converts it into scintillator light. For this reason, an X-ray image based on high-energy X-rays is created by applying various image processings to the X-ray detection signal output from the photodetection panel 7. That is, the X-ray detector 1 is a dual energy type X-ray detector, and it is possible to obtain both the X-ray image based on low-energy X-rays and the X-ray image based on high-energy X-rays using the X-ray detector 1 by irradiating X-rays once. The scintillator element 19 corresponds to a second scintillator element according to the invention.

As a characteristic of the invention, the light blocking wall 17 provided in the scintillator panel 9 and the light blocking wall 21 provided in the scintillator panel 13 are not aligned with each other in the X-ray incidence direction indicated by a reference symbol "R." That is, according to the first embodiment, a grid pattern of the light blocking wall 17 indicated by the solid line and a grid pattern of the light blocking wall 21 indicated by the dotted line are arranged to deviate from each other along the X-ray incidence face (x-y plane) as illustrated in the plan view of FIG. 2. As a result, the scintillator element 19 is arranged to deviate from a position linked to the scintillator element 15. In the configuration of the first embodiment, each grid pattern is configured to deviate along the x-y plane. Therefore, as illustrated in FIG. 3, the light blocking walls 17 and 21 are arranged to be staggered from each other. That is, in the configuration of the first embodiment, an X-ray P incident to the X-ray detector 1 from the direction indicated by the reference symbol R is necessarily incident to at least one of the scintillator elements 15 and the 19. For this reason, the X-ray P is more reliably converted into the scintillator light and are detected by the pixel 25 or 29. Therefore, it is possible to more reliably avoid the X-ray P from passing through the X-ray detector 1 without being detected. Therefore, it is possible to improve X-ray sensitivity of the X-ray detector.

The X-ray detector 1 according to the first embodiment has a stacked structure obtained by stacking the photodetection panel 5, the scintillator panel 9, the substrate 11, the scintillator panel 13, and the photodetection panel 7 sequentially in this order in the X-ray irradiation direction. In addition, according to the first embodiment, there is no particular limitation in a process of manufacturing the X-ray detector 1 by combining each configuration as long as the stacked structure is provided as described above, and the grid pattern of the light blocking wall 17 and the grid pattern of the light blocking wall 21 deviate from each other along the X-ray incidence face. However, the X-ray detector 1 is preferably manufactured through the following process.

First, a planar substrate 11 is prepared (FIG. 4(a)). In addition, the light blocking walls 17 are formed on one surface of the substrate 11 in a grid shape (step S1), and the light blocking walls 21 are formed on the other surface of the substrate 11 in a grid shape (step 2, FIG. 4(b)). Note that, since the process of forming the light blocking walls 17 and 21 on the substrate 11 is discussed in Patent Literature 2 in details, the description thereof will not be repeated herein.

Through the process of steps S1 and S2, each of the light blocking walls 17 and 21 is formed integrally by interposing the substrate 11. For this reason, it is possible to accurately form each of the light blocking walls 17 and 21 in expected positions on the substrate 11. Therefore, it is possible to accurately form the grid pattern of the light blocking walls 17 and the grid pattern of the light blocking walls 21 in the expected positions by deviating from each other along the x-y plane.

Using each of the light blocking walls 17 and 21 having the grid shape, cells partitioned in a two-dimensional matrix shape are formed on both surfaces of the substrate 11. Then, the scintillator elements 15 are filled in the cells partitioned by the light blocking walls 17 (step S3). The scintillator panel 9 is formed by filling the scintillator elements 15. In addition, the scintillator panel 13 is formed by filling the scintillator elements 19 in the cells partitioned by the light blocking walls 21 (step S4). As the scintillator panels 9 and 13 are formed on both surfaces of the substrate 11, the scintillator block 3 is formed (FIG. 4 (c)).

After forming the scintillator block 3, the photodetection panel 5 is bonded to the scintillator panel 9 (step S5). In addition, the photodetection panel 7 is bonded to the scintillator panel 13 (step S6). As each of the photodetection panels 5 and 7 is combined with the scintillator block 3, a dual energy type X-ray detector 1 is manufactured (FIG. 4(d)).

Note that, since the light blocking walls are provided in each of the scintillator panels, a positional deviation of the photodetection panel is allowed within a predetermined range depending on a thickness of the light blocking wall when each photodetection panel is combined with each scintillator panel. For this reason, it is possible to more appropriately avoid occurrence of a trouble in the X-ray detector 1 caused by misalignment of the photodetection panel when the photodetection panel is combined. An allowable range of the positional deviation in the positioning of the photodetection panel will be described below in more details.

Here, operations performed for dual energy imaging using the X-ray detector 1 according to the first embodiment will be described with reference to FIG. 5. In the X-ray imaging, X-rays are irradiated in the direction indicated by the reference symbol "R." First, the X-rays transmit through the photodetection panel 5 and are incident to the scintillator panel 9. Out of the X-rays incident to the scintillator panel 9, a high-energy X-ray P2 passes through the scintillator panel 9 without being absorbed to the scintillator element 15. In addition, the high-energy X-ray P2 incident to the scintillator panel 13 is absorbed in the scintillator element 19 and is converted into scintillator light Q2. The scintillator light Q2 is converted into electric charges as an electric signal by the pixel 29, and the electric signal is output as an X-ray detection signal.

Out of low-energy X-rays P1 having energy lower than that of the X-ray P2, an X-ray P1a incident to the scintillator element 15 of the scintillator panel 9 is converted into scintillator light Q1a by the scintillator element 15. The scintillator light Q1a is converted into an electric signal by the pixel 25 and is output as an X-ray detection signal.

Meanwhile, out of the low-energy X-rays P1, an X-ray P1b incident to the light blocking wall 17 of the scintillator panel 9 passes through the scintillator panel 9 without being absorbed in the scintillator element 15. However, since the grid pattern deviates along the x-y plane, the light blocking walls 17 and 21 are not aligned straightly in the z-direction as an X-ray irradiation direction. For this reason, the low-energy X-ray P1b is not incident to the light blocking wall 21 of the scintillator panel 13, but is incident to the scintillator element 19. In addition, the X-ray P1b is converted into scintillator light Q1b in the scintillator element 19 and is output as an X-ray detection signal from the pixel.

In this manner, the grid pattern of the light blocking walls 17 and the grid pattern of the light blocking walls 21 deviate from each other on the x-y plane. Therefore, an X-ray incident to the X-ray detector 1 is converted into scintillator light in at least one of the scintillator panels. Therefore, it is possible to reduce an area where it is difficult to detect an X-ray in the X-ray detector and thus remarkably improve the X-ray sensitivity of the dual energy type X-ray detector.

Effects in Configuration of First Embodiment

In this manner, the dual energy type X-ray detector 1 according to the first embodiment includes scintillator elements 15 partitioned by the light blocking walls 17 to convert the low-energy X-rays into light and scintillator elements 19 partitioned by the light blocking walls 21 to convert high-energy X-rays into light. In addition, the light blocking walls 17 and 21 are formed such that positions of the grid-like patterns deviate from each other on the x-y plane. In this case, as seen in the X-ray incidence direction, an area where the light blocking walls 17 and 21 are overlapped with each other is remarkably reduced. That is, the light blocking walls 17 and 21 are not aligned straightly in the X-ray incidence direction.

In the configuration of the first embodiment, the light blocking walls 17 and 21 are arranged to be staggered from each other as illustrated in FIG. 3. Therefore, an X-ray P is converted into light by at least one of the scintillator elements, and the X-ray detection signal is finally output. That is, even when the light blocking walls are formed in the X-ray detector 1, it is possible to remarkably reduce an area where it is difficult to detect an X-ray in the X-ray detector. Therefore, using the light blocking wall, it is possible to increase a resolution of the X-ray image and improve the X-ray sensitivity of the X-ray detector.

In the dual energy type X-ray detector of the related art, a first substrate provided with a scintillator panel for detecting low energy and a second substrate provided with a scintillator panel for detecting high energy are bonded. In this case, since their positions deviate from each other in the bonding process, it is difficult to accurately position each scintillator panel. Therefore, when the configuration in which the scintillator elements are partitioned by the light blocking walls is employed in the dual energy type X-ray detector of the related art, the positions of the light blocking walls provided in each scintillator panel easily deviate from the expected positions. As a result, positions of the images projected onto each X-ray image obtained through the dual energy imaging are not aligned with each other. Therefore, diagnostic performance of the X-ray image is seriously degraded. In addition, although the grid patterns of the light blocking walls are expected to deviate from each other, the grid patterns of the light blocking walls may be aligned with each other along the x-y plane due to a positional deviation of the light blocking wall.

Meanwhile, the X-ray detector 1 according to the first embodiment has the scintillator panel 9 provided on one surface of the substrate 11 and the scintillator panel 13 provided on the other surface of the substrate 11. That is, the grid patterns of the light blocking walls 17 and 21 are formed on a single substrate. Therefore, it is possible to more accurately form the light blocking walls 17 and 21 in corresponding expected positions. As a result, it is possible to improve the X-ray sensitivity of the X-ray detector 1 as expected. Therefore, it is possible to perform the dual energy imaging with higher diagnostic performance using the X-ray detector 1.

In the dual energy type X-ray detector according to the first embodiment, the pitches of the light blocking walls 17 and 21 may be set to a short length of approximately 60 to 150 μm. For this reason, it is possible to apply the dual energy imaging to an X-ray imaging method that requires a short pitch of the pixel, such as X-ray CT imaging. In addition, in the dual energy imaging, it is possible to obtain an X-ray image having a higher resolution.

In the X-ray detector 1 according to the first embodiment, the single substrate 11 is employed. That is, compared to a configuration of the related art in which a pair of substrates are bonded, it is possible to reduce the thickness of the X-ray detector using the configuration according to the first embodiment. Therefore, it is possible to more appropriately avoid degradation of compatibility and versatility of the dual energy type X-ray detector according to the first embodiment.

In the X-ray detector 1 according to the first embodiment, each scintillator panel has a configuration in which the scintillator elements of each scintillator panel are partitioned by the light blocking walls. For this reason, in the process of manufacturing the X-ray detector 1, it is possible to more appropriately avoid occurrence of a trouble caused by a positional deviation of the photodetection panel when the photodetection panels 5 and 7 are combined with the scintillator block 3. An allowable range of the positional deviation of the photodetection panel will now be described with reference to each of FIGS. 6(a) to 6(d).

In order to improve the diagnostic performance of the X-ray image, it is ideal that the scintillator light emitted from a single scintillator element be entirely incident to the same pixel. That is, it is ideal that the positioning be accurately performed such that each position of the pixel 25 is accurately aligned with the position of the scintillator element 15 when the photodetection panel 5 is combined with the scintillator block 3.

A structure of the X-ray detector 1 manufactured through accurate positioning in a configuration in which no light blocking wall is provided on the scintillator panel is illustrated in FIG. 6(a) by way of example. In this case, the length of the pixel 25 in an x-direction is substantially equal to the length of the scintillator element 15 in the x-direction. For this reason, the scintillator light emitted from the scintillator element 15a is entirely incident to a pixel 25a. Note that an asterisk mark is added to a right end position of the pixel 25a.

Here, the position of the photodetection panel 5 may deviate when the photodetection panel 5 is combined with the scintillator block 3. In a configuration of the dual energy type X-ray detector of the related art in which no light blocking wall 17 is provided, the photodetection panel 5 deviates in the x-direction as indicated by an arrow symbol. Therefore, the scintillator light Q1 emitted from the scintillator element 15a is detected by the pixels 25a and 25b (FIG. 6(b)).

That is, in the configuration in which no light blocking wall is provided in the scintillator panel, the scintillator light Q1 emitted from a single scintillator element is easily detected by a plurality of pixels in many cases just by slightly deviating the photodetection panel 5 in the x-direction. That is, in the configuration of the related art in which no light blocking wall is provided in the scintillator panel, an allowable range of the positional deviation in the positioning of the photodetection panel 5 is very narrow.

Meanwhile, a structure of the X-ray detector 1 manufactured through accurate positioning in the first embodiment is illustrated in FIG. 6(c) by way of example. In this case, the length of the pixel 25 in the x-direction is approximately equal to a length obtained by adding a thickness N of the light blocking wall 17 and the length of the scintillator element 15 of the x-direction. For this reason, the scintillator light emitted from the scintillator element 15a is entirely incident to the pixel 25a.

In the configuration of the first embodiment in which the light blocking wall 17 is provided, even when the position of the photodetection panel 5 deviates in the x-direction by a length corresponding to the thickness N of the light blocking wall 17, the scintillator light Q1 emitted from a scintillator element 15a is entirely incident to the pixel 25a (FIG. 6(d)). That is, in the X-ray detector 1 according to the first embodiment, there is an allowable range for the positional deviation of the photodetection panel 5 depending on the thickness N of the light blocking wall 17 when the photodetection panel 5 is positioned.

Such an allowable range for the positional deviation is provided in both a case where the positioning of the photodetection panel 5 is performed in the y-direction and a case where the positioning between the photodetection panel 7 and the scintillator block 3 is performed. Therefore, according to the first embodiment, since the scintillator elements are partitioned by the light blocking walls, it is possible to more appropriately avoid occurrence of a trouble of the X-ray detector 1 caused by a positional deviation of the photodetection panel.

Second Embodiment

Next, a second embodiment of the invention will be described with reference to the accompanying drawings. FIG. 7(a) is a cross-sectional view illustrating a configuration of a dual energy type X-ray detector 1A according to the second embodiment. Note that like reference numerals denote like elements as in the first embodiment, and they will not be described repeatedly.

Similar to the first embodiment, the X-ray detector 1A according to the second embodiment has a stacked structure obtained by stacking a photodetection panel 5, a scintillator block 3, and a photodetection panel 7 sequentially in this order in the z-direction. However, the scintillator block 3 according to the second embodiment is different from the first embodiment in that the substrate 11 is not provided. That is, according to the second embodiment, a stacked structure has the scintillator panels 9 and 13 directly bonded to each other. In addition, similar to the first embodiment, each of the scintillator panels 9 and 13 is preferably covered by a light reflection film formed of aluminum or the like. In this case, in the X-ray detector 1A, the scintillator panels 9 and 13 covered with the light reflection film are directly stacked.

Similar to the first embodiment, the light blocking walls 17 of the scintillator panel 9 and the light blocking walls 21 of the scintillator panel 13 are not aligned with each other in the X-ray incidence direction indicated by the reference symbol R. That is, the grid pattern of the light blocking wall 17 on the X-ray incidence face (x-y plane) deviates from the grid pattern of the light blocking wall 21 on the x-y plane (refer to FIG. 2). Therefore, the light blocking walls 17 and 21 are not aligned straightly in the z-direction, but are arranged in a staggered manner.

The X-ray detector 1A according to the second embodiment has a stacked structure obtained by stacking a photodetection panel 5, a scintillator panel 9, a scintillator panel 13, and a photodetection panel 7 sequentially in this order in the X-ray irradiation direction. Note that, according to the second embodiment, there is no particular limitation in the process of manufacturing the X-ray detector 1A by combining each configuration as long as the stacked structure is provided as described above, and the grid pattern of the light blocking wall 17 and the grid pattern of the light blocking wall 21 deviate from each other along the X-ray incidence face. However, the X-ray detector 1A is preferably manufactured through the following process.

First, a photodetection panel 5 having a planar substrate 23 obtained by arranging pixels 25 is prepared (FIG. 8(a)). In addition, the light blocking walls 17 are formed on one surface of the substrate 11 in a grid shape (step S1, FIG. 8(b)). Then, scintillator elements 15 are filled in cell spaces partitioned by the light blocking walls 17 (step S2). By filling the scintillator elements 15, a scintillator panel 9 is formed. An assembly obtained by stacking the scintillator panel 9 and the photodetection panel 5 corresponds to a panel assembly 31 (FIGS. 7(b) and 8(c))

Through a process similar to that of the panel assembly 31, a panel assembly 33 is formed by providing the scintillator panel 13 on one surface of the photodetection panel 7. That is, the light blocking walls 21 are formed on one surface of the photodetection panel 7 having a planar substrate 27 provided with pixels 29 in a grid shape (step 3). Then, the scintillator elements 19 are filled in the cell spaces partitioned by the light blocking walls 21 (step S4). By filling the scintillator elements 19, the scintillator panel 13 is formed. Through the process of steps S3 and S4, a panel assembly 33 as an assembly formed by stacking the scintillator panel 13 and the photodetection panel 7 is obtained. In addition, the sequence of steps S1 to S4 may be appropriately changed as necessary.

After the panel assemblies 31 and 33 are formed, the panel assemblies 31 and 33 are combined with each other while the scintillator panels 9 and 13 face each other (step S5, FIG. 8(d)). In step S5, the scintillator panels 9 and 13 are combined such that the grid pattern of the light blocking wall 17 and the grid pattern of the light blocking wall 21 deviate from each other along the x-y plane.

By combining the panel assemblies 31 and 33, an X-ray detector 1A in which the scintillator panels 9 and 13 are directly stacked is manufactured. Unlike the first embodiment, the X-ray detector 1A has a structure having no substrate 11. For this reason, according to the second embodiment, it is possible to further reduce the thickness of the X-ray detector 1A. Therefore, it is possible to improve compatibility and versatility of the X-ray detector 1A.

In this manufacturing method, instead of bonding the photodetection panel and the scintillator panel, the scintillator panel is formed directly on the photodetection panel. Therefore, it is possible to avoid misalignment that may occur during the bonding. Therefore, it is possible to more appropriately avoid the pixels and the light blocking walls from deviating from the expected positions.

The process of performing dual energy imaging using the X-ray detector 1A is similar to that of the first embodiment. That is, as illustrated in FIG. 7(a), first, the X-rays irradiated from the direction indicated by the reference symbol R pass through the photodetection panel 5 and are incident to the scintillator panel 9. In addition, out of the X-rays incident to the scintillator panel 9, the high-energy X-ray P2 passes through the scintillator element 15 and is absorbed in the scintillator element 19. Out of the low-energy X-rays P1, the X-ray P1a incident to the scintillator element 15 is absorbed in the scintillator element 15.

Meanwhile, the X-ray P1b incident to the light blocking wall 17 passes through the scintillator panel 9. However, since the light blocking walls 17 and 21 are not aligned straightly in the z-direction, the X-ray P1b incident to the scintillator panel 13 is appropriately absorbed in the scintillator element 19. Therefore, similar to the first embodiment, it is possible to remarkably reduce the area where the X-ray is not detected in the X-ray detector 1A.

In this manner, similar to the first embodiment, the X-ray detector 1A according to the second embodiment is configured such that the grid pattern of the light blocking walls 17 and the grid pattern of the light blocking walls 21 deviate from each other along the X-ray incidence face. For this reason, it is possible to remarkably reduce an area where it is difficult to detect an X-ray in the X-ray detector. Therefore, it is possible to remarkably improve the X-ray sensitivity of the X-ray detector 1A. Furthermore, in the X-ray detector 1A, the scintillator panels 9 and 13 are bonded directly. That is, compared to the X-ray detector 1 of the first embodiment, it is possible to reduce the thickness of the X-ray detector 1A by omitting the substrate 11. For this reason, it is possible to more improve compatibility and versatility of the X-ray detector 1A. In addition, since the thickness of the X-ray detector is reduced, it is possible to more appropriately avoid scattering of the scintillator light. Therefore, it is possible to improve the resolution of the X-ray image obtained by the X-ray detector 1A.

Third Embodiment

Next, a third embodiment according to the invention will be described with reference to the accompanying drawings. FIG. 9(a) is a cross-sectional view illustrating a configuration of the X-ray detector 1B according to the third embodiment.

Similar to the second embodiment, the substrate 11 is not provided in the third embodiment. However, the third embodiment is different from the second embodiment in that the sequence of stacking the photodetection panel 5 and the scintillator panel 9 is reversed. Specifically, in the X-ray detector 1B according to the third embodiment, the scintillator panel 9, the photodetection panel 5, the scintillator panel 13, and the photodetection panel 7 are stacked sequentially in this order.

Similar to other embodiments, in the X-ray detector 1B, the grid pattern of the light blocking wall 17 provided in the scintillator panel 9 and the grid pattern of the light blocking wall 21 provided in the scintillator panel 13 deviate from each other along the x-y plane (refer to FIG. 2). Therefore, the light blocking walls 17 and 21 are not aligned straightly in the z-direction, but are arranged in a staggered manner. For this reason, an X-ray incident to the X-ray detector 1B is reliably incident to the scintillator element 15 or the 19 regardless of the energy level. As a result, since the area where the X-ray is not detected in the X-ray detector 1B is significantly reduced, it is possible to improve the X-ray sensitivity of the X-ray detector 1B.

There is no particular limitation in the process of manufacturing the X-ray detector 1B by combining each configuration. However, the X-ray detector 1B is preferably manufactured through the following process.

First, a photodetection panel 5 having a planar substrate 23 obtained by arranging pixels 25 on one surface is prepared (FIG. 10(a)). In addition, the light blocking walls 17 are formed on one surface of the photodetection panel 5, that is, a surface where the pixels 25 are arranged in a grid shape (step S1). Then, the light blocking walls 21 are formed on the other surface of the photodetection panel 5 in a grid shape (step 2, FIG. 10(b))

Through the process of steps S1 and S2, each of the light blocking walls 17 and 21 is formed integrally by interposing the photodetection panel 5. For this reason, it is possible to accurately form each of the light blocking walls 17 and 21 in expected positions on the substrate 11. Therefore, it is possible to more reliably form a configuration in which the grid pattern of the light blocking walls 17 and the grid pattern of the light blocking walls 21 deviate from each other along the x-y plane.

Using each of the light blocking walls 17 and 21 having the grid shape, cells partitioned in a two-dimensional matrix shape are formed on both surfaces of the photodetection panel 5. Then, the scintillator elements 15 are filled in the cell spaces partitioned by the light blocking walls 17 (step S3). The scintillator panel 9 is formed by filling the scintillator elements 15. In addition, the scintillator panel 13 is formed by filling the scintillator elements 19 in the cell spaces partitioned by the light blocking walls 21 (step S4). As the scintillator panels 9 and 13 are respectively formed on both surfaces of the photodetection panel 5, a scintillator assembly 35 is provided (FIGS. 9(b) and 10(c)).

After forming the scintillator assembly 35, the scintillator assembly 35 is combined with the photodetection panel 7 by bonding the photodetection panel 7 to the scintillator panel 13 (step S5). A dual energy type X-ray detector 1B is manufactured by combining the scintillator assembly 35 and the photodetection panel 7 (FIG. 10(d)). Similar to the second embodiment, the X-ray detector 1B has a structure having no substrate 11. For this reason, according to the third embodiment, it is possible to further reduce the thickness of the X-ray detector 1B. Therefore, it is possible to improve compatibility and versatility of the X-ray detector 1B.

When the dual energy imaging is performed in the first and second embodiments, the X-rays are first incident to the photodetection panel 5. In this configuration, since the X-rays are incident directly to the photodetection panel 5, the photodetection panel 5 is relatively easily deteriorated. Meanwhile, when the dual energy imaging is performed using the X-ray detector 1B, the X-rays irradiated in the direction indicated by the reference symbol R are first incident to the scintillator panel 9. In this configuration, since the X-rays are not directly incident to the photodetection panel 5, it is possible to delay a deterioration rate of the photodetection panel 5 according to the third embodiment, compared to the first and second embodiments.

In the X-ray detector 1B according to the third embodiment, the scintillator panels 9 and 13 are integrated as the scintillator assembly 35. That is, the scintillator panel 9 is formed on one surface of the photodetection panel 5, and the scintillator panel 13 is formed on the other surface of the photodetection panel 5. In this case, the light blocking walls 17 and 21 are formed in pattern on a single photodetection panel 5. Therefore, it is possible to more accurately form each of the light blocking walls 17 and 21 in expected positions. As a result, using the X-ray detector 1B, it is possible to perform dual energy imaging with higher diagnostic performance.

Fourth Embodiment

FIG. 11 illustrates an X-ray detector according to a fourth embodiment. The X-ray detector according to the fourth embodiment corresponds to the X-ray detector according to the second embodiment of FIGS. 7(a) and 7(b) for convenient description purposes. However, this may similarly apply to other configurations of the first and third embodiments.

The fourth embodiment is characterized in that the light blocking walls 17 provided in the scintillator panel 9 and the light blocking walls 21 provided in the scintillator panel 13 are aligned with the X-ray incidence direction. That is, according to the fourth embodiment, the grid pattern of the light blocking wall 17 and the grid pattern of the light blocking wall 21 are aligned with each other along the X-ray incidence face (x-y plane) as illustrated in a plan view of FIG. 11. Therefore, the light blocking walls 21 of the scintillator panel 13 are seen as extending from the light blocking walls 17 of the scintillator panel 9. Since the grid pattern of the light blocking walls 17 and the grid pattern of the light blocking walls 21 are aligned with each other, the scintillator element 19 is arranged to link to the scintillator element 15. Similarly, according to the fourth embodiment, the scintillator elements are partitioned by the light blocking walls as described in the first embodiment. Therefore, it is possible to more appropriately avoid occurrence of a trouble in the X-ray detector caused by a positional deviation of the photodetection panel.

FIG. 12 illustrates a unique effect of the configuration of the fourth embodiment. When the dual energy imaging is performed, an X-ray source emits both the high-energy X-rays P2 and the low-energy X-rays P1. As illustrated in FIG. 12, the low-energy X-ray P1 does not transmit through the near-side panel assembly 31 with respect to the X-ray source and is detected by the near-side panel assembly 31. The high-energy X-ray P2 transmits through the panel assembly 31 and is detected by the far-side panel assembly 32 with respect to the X-ray source. In the X-ray detector according to the invention, it is assumed that the X-ray detected by the panel assembly 31 is the low-energy X-rays, and the X-ray detected by the panel assembly 32 is the high-energy X-ray. Therefore, in order to accurately distinguish the energy of the detected X-rays, it is ideal that all of the low-energy X-rays be detected by the panel assembly 31, and all of the high-energy X-rays be detected by the panel assembly 32.

As described in the second embodiment, when the grid patterns are different from each other, the energy of the detected X-rays is not accurately distinguished. FIG. 13 illustrates this situation. FIG. 13 is a diagram enlargedly illustrating a portion where the scintillator panels 9 and 13 are linked to each other in the X-ray detector according to the second embodiment. The light blocking walls 17 provided in the scintillator panel 9 have a certain level of thickness even though it is thin. Since the light blocking walls 17 are formed of a reflecting material capable of reflecting fluorescent light, a capability of blocking the X-ray is not sufficiently high. Therefore, a low-energy X-ray incident to the light blocking wall 17 of the scintillator panel 9 passes through the light blocking wall 17 and is directed to the scintillator panel 13. In the configuration of the second embodiment, since the grid pattern of the light blocking walls 17 and the grid pattern of the light blocking walls 21 deviate from each other, the light blocking walls 17 adjoin the scintillator elements 19 of the scintillator panel 13. Therefore, the low-energy X-ray passing through the light blocking walls 17 of the scintillator panel 9 is incident to the scintillator elements 19 of the scintillator panel 13 and is converted into fluorescent light by the scintillator element 19. This fluorescent light is detected by the panel assembly 32. The panel assembly 32 detects a part of the low-energy X-rays as well although the panel assembly 32 ideally detects only the high-energy X-ray.

FIG. 14 illustrates an X-ray detector according to the fourth embodiment. In the configuration of the fourth embodiment, since the grid pattern of the light blocking walls 17 and the grid pattern of the light blocking walls 21 are aligned with each other, the light blocking walls 17 adjoin the light blocking walls 21 of the scintillator panel 13. Therefore, a low-energy X-ray passing through the light blocking wall 17 of the scintillator panel 9 is incident to the light blocking wall 21 of the scintillator panel 13 and directly passes through the scintillator panel 13. This X-ray is not detected by the panel assembly 32. The panel assembly 32 ideally operates to detect only a high-energy X-ray. In this manner, in the configuration of the fourth embodiment, it is possible to provide an X-ray detector having a high energy resolution.

The invention is not limited to the aforementioned embodiments and may be modified as described below.

(1) In manufacturing process of the first embodiment described above, the scintillator panels 9 and 13 are integrally formed on both surfaces of a single substrate 11. Alternatively, the substrate 11 may include a pair of substrates 11a and 11b bonded to each other. A process of manufacturing an X-ray detector 1C according to a modification of the first embodiment will be described below with reference to each drawing of FIGS. 15(a) to 15(d).

First, light blocking walls 17 are formed on one surface of a planar substrate 11a in a grid shape (step S1, FIG. 15(a)). Meanwhile, light blocking walls 21 are formed on one surface of a planar substrate 11b in a grid shape (step S2, FIG. 15(a)). Then, the scintillator elements 15 are filled in cell spaces partitioned by the light blocking walls 17 (step S3). By filling the scintillator elements 15, a scintillator panel 9 is formed (FIG. 15(b)). In addition, the scintillator elements 19 are filled in the cell spaces partitioned by the light blocking walls 21 (step S4). By filling the scintillator elements 19, a scintillator panel 13 is formed (FIG. 15(b)).

Then, a scintillator block 3 is formed by bonding the substrate 11a provided with the scintillator panel 9 and the substrate 11b provided with the scintillator panel 13 (step S5, FIG. 15(c)). In step S5, while the other surface of the substrate 11*a* and the other surface of the substrate 11*b* face each other, positioning is performed such that the grid pattern of the light blocking walls 17 and the grid pattern of the light blocking walls 21 deviate from each other along the x-y plane, and the substrates 11*a* and 11*b* are bonded to each other.

After the scintillator block 3 is formed, the photodetection panel 5 is bonded to the scintillator panel 9 (step S6). In addition, the photodetection panel 7 is bonded to the scintillator panel 13 (step S7). By combining the photodetection panels 5 and 7 with the scintillator block 3, a dual energy type X-ray detector 1C is manufactured (FIG. 4(*d*)).

In the configuration of modification (1) as a modification of the first embodiment, a pair of assemblies are formed by stacking the substrate, the scintillator panel, and the photodetection panel, and the substrates are then bonded to each other to combine the pair of assemblies. In this case, the grid-like light blocking wall is formed on one surface of each of the two substrates. That is, a process of forming the light blocking walls on both surfaces of the substrate is not necessary. Therefore, when the manufacturing process according to the modification of the first embodiment is employed, it is possible to avoid the X-ray detector manufacturing process from becoming complicated. For this reason, it is possible to reduce a manufacturing cost of the X-ray detector 1 as a dual energy type X-ray detector provided with the light blocking walls.

(2) In each of the embodiments described above, the scintillator elements are partitioned in a square shape by the grid-like light blocking wall 17 (or light blocking wall 21). However, the partitioning shape is not limited to the square shape. Alternatively, as other example of the cell shape partitioned by the light blocking wall 17, various shapes such as rectangular, parallelogram, trapezoidal, and hexagonal shapes may also be selected appropriately.

(3) In each embodiment described above, the pitch of the pixel 25 for detecting the scintillator light based on low-energy X-rays and a pitch of the pixel 29 for detecting the scintillator light based on high-energy X-rays are substantially equal to each other. However, the invention is not limited thereto. Alternatively, the pitch of the pixel 25 may be different from the pitch of the pixel 29. In particular, considering existence of an X-ray incident obliquely with respect to the X-ray incidence face of the X-ray detector 1, it is preferable that the pitch of the pixel 29 be larger than the pitch of the pixel 25.

(4) In each of the embodiments described above, the pitch of the light blocking wall 17 is equal to the pitch of the light blocking wall 21 as illustrated in FIG. 2 or the like. However, the invention is not limited thereto. That is, the pitch of the light blocking wall 17 may be different from the pitch of the light blocking wall 21. In particular, as illustrated in FIG. 16(*a*), it is preferable that the grid pattern of the light blocking wall 17 and the grid pattern of the light blocking wall 21 deviate from each other along the x-y plane while the pitch of the light blocking wall 21 is larger than the pitch of the light blocking wall 17. In FIG. 16(*a*), the pitch of the light blocking wall 21 is set to twice the pitch of the light blocking wall 17 by way of example.

FIG. 16(*b*) is a cross-sectional view illustrating an X-ray detector 1D according to such a modification (4). In the configuration of this modification, the number of light blocking walls 21 is smaller than the number of the light blocking walls 17. Out of the high-energy X-rays P2 incident to the X-ray detector, the X-ray P2*a* incident to the scintillator element 19 is appropriately converted into scintillator light Q2 by the relatively thick scintillator element 19. In addition, the scintillator light Q2 is converted into an electric charge by the pixel 29, and the electric charge is detected.

Meanwhile, the X-ray P2*b* incident to the light blocking walls 21 out of the high-energy X-rays P2 is not converted into the scintillator light in the scintillator panel 13. In addition, the scintillator element 15 is not allowed to covert the high-energy X-rays P2. For this reason, in the area where the light blocking walls 21 are provided, the X-ray detector can detect the low-energy X-ray P1, whereas it is difficult to detect the high-energy X-ray P2*b*.

In this regard, in the X-ray detector 1D according to the modification (4), the number of light blocking walls 21 is reduced relative to the number of light blocking walls 17 by increasing the pitch of the light blocking wall 21 or any other method. In this configuration, it is possible to more reduce the high-energy X-rays P2*b* incident to the light blocking wall 21. For this reason, it is possible to reduce an area where it is difficult to detect high-energy X-rays in the X-ray detector.

The X-rays incident to the light blocking walls 17 of the scintillator panel 9 are certainly incident to the scintillator elements 19 of the scintillator panel 13. Therefore, in the area where the light blocking walls 17 are formed, the X-ray detector can detect X-rays regardless of the energy level. As a result, by more reducing the number of light blocking walls 21 relative to the number of the light blocking walls 17, the area where an X-ray can be detected is widened regardless of the energy level. Therefore, it is possible to further improve the X-ray sensitivity of the X-ray detector.

(5) In each of the embodiments described above, the scintillator elements are partitioned by the light blocking walls that block the scintillator light. However, the configuration for partitioning the scintillator elements is not limited to the light blocking walls. Alternatively, as illustrated in FIG. 17, the scintillator elements 15 may be partitioned by tunneling grid-shaped trenches in the scintillator elements 15 in the z-direction. The scattering of the scintillator light emitted from the scintillator elements 15 may be disturbed by a trench F. Therefore, similar to the configuration of the light blocking wall, it is possible to avoid the scintillator light from scattering to the neighboring scintillator elements 15 using the configuration in which the trenches F are formed in the scintillator elements as well. In such an X-ray detector 1E according to a modification (5), the trench F corresponds to a light blocking portion according to the invention.

In addition, the trenches F of the scintillator elements 15 are not straightly aligned with the trenches F of the scintillator elements 19 in the X-ray incidence direction (z-direction). In this manner, since the trenches F of the scintillator elements 15 and the trenches F of the scintillator elements 19 are formed to be staggered from each other with respect to the X-ray incidence face, the X-rays incident to the X-ray detector are reliably converted into light by the scintillator elements 15 or 19. Therefore, it is possible to reduce an area where it is difficult to detect an X-ray in the X-ray detector and improve the X-ray sensitivity.

(6) In each of the embodiments described above, an indirect conversion type X-ray detector has been described by way of example, in which the X-rays are converted into light using the scintillator element or the like, and the light is further converted into an electric signal. Alternatively, the configuration according to the invention may also be applied to a direct conversion type X-ray detector in which the X-rays are directly converted into an electric signal. Specifically, in the configurations of each embodiment, an X-ray conversion element formed of amorphous selenium (a-Se) to convert X-rays into electric charges may be employed instead of the scintillator element. In addition, instead of the light blocking wall, a blocking wall (or trench) capable of blocking scattering of electric charges may be formed in a grid shape, so that it is possible to obtain the same effects as those of the invention using the direct conversion type X-ray detector. In such a direct conversion and dual energy type X-ray detector according to a modification (6), the blocking wall (or trench) corresponds to a blocking portion of the invention.

A configuration of a direct conversion and dual energy type X-ray detector 1F according to the modification (6) is illustrated in FIG. 18. The X-ray detector 1F is obtained by employing a direct conversion configuration in the indirect conversion and dual energy type X-ray detector 1 of the first embodiment. In addition, like reference numerals denote like elements as in the configuration of the X-ray detector 1.

The X-ray detector 1F has a stacked structure obtained by stacking an X-ray detection panel 37, an X-ray conversion layer 39, a substrate 11, an X-ray conversion layer 41, and an X-ray detection panel 43 sequentially in this order. The X-ray detection panel 37 has a substrate 23 and pixels 25A arranged in a two-dimensional matrix shape. The X-ray detection panel 37 corresponds to a first X-ray detection panel according to the invention. The X-ray detection panel 43 corresponds to a second X-ray detection panel according to the invention.

The X-ray conversion layer 41 has a substrate 27 and pixels 29A arranged in a two-dimensional matrix shape. The X-ray conversion layer 39 is shaped such that X-ray conversion elements 45 arranged in a two-dimensional matrix shape are partitioned by grid-like blocking walls 47. The X-ray conversion layer 41 is shaped such that X-ray conversion elements 49 arranged in a two-dimensional matrix shape are partitioned by grid-like blocking walls 51. The X-ray conversion layer 39 corresponds to a first X-ray conversion layer according to the invention. The X-ray conversion layer 41 corresponds to a second X-ray conversion layer according to the invention. The X-ray conversion element 45 corresponds to a first X-ray conversion element according to the invention. The X-ray conversion element 49 corresponds to a second X-ray conversion element according to the invention.

Each of the X-ray conversion elements 45 and 49 is formed of a-Se or the like to convert incident X-rays into electric charges. Each of the blocking walls 47 and 51 is formed of a material capable of blocking movement of electric charges to prevent scattering of the electric charges. The grid pattern of the blocking wall 47 and the grid pattern of the blocking wall 51 are configured to deviate from each other along the X-ray incidence face. The blocking walls 47 and 51 may be a trench portion capable of preventing scattering of electric charges. The blocking wall 47 corresponds to a first blocking portion according to the invention. The blocking wall 51 corresponds to a second blocking portion according to the invention.

Unlike the pixels 25 and 29, the pixels 25A and 29A have no photoelectric conversion element. That is, the pixels 25A and 29A detect electric charges converted by the X-ray conversion element and output the electric charges as an X-ray detection signal. The X-ray conversion element 45 converts X-rays having relatively low energy into electric charges. For this reason, an X-ray image based on low-energy X-rays is created by applying various image processings to the X-ray detection signal output from the pixels 25A of the X-ray detection panel 37.

Meanwhile, the X-ray conversion element 49 converts X-rays having relatively high energy into electric charges. For this reason, an X-ray image based on high-energy X-rays is created by applying various image processings to the X-ray detection signal output from the pixels 25A of the X-ray detection panel 43. Note that the direct conversion type configuration of the modification (6) may be applied to indirect conversion and dual energy type X-ray detectors of other embodiments and modifications.

(7) In each of the embodiments described above, it is preferable that the pitch of the light blocking wall 17 (or light blocking wall 21) be substantially equal to the pitch of the pixel 25 (or pixel 29). However, the invention is not limited thereto. As another preferable configuration, the pitch of the light blocking wall may be an integer multiple of the pitch of the pixel. Alternatively, the pitch of each light blocking wall may not be an integer multiple of the pitch of the pixel as long as the grid pattern of the light blocking wall 17 and the grid pattern of the light blocking wall 21 deviate from each other along the x-y plane.

(8) In the configurations of the embodiments described above, the light blocking walls 21 are provided in the scintillator panel 13. However, the invention is not limited thereto. As illustrated in FIG. 19, the light blocking wall 21 may not be provided in the scintillator panel 13. For convenient description purposes, the X-ray detector according to this modification corresponds to the X-ray detector of the fourth embodiment of FIG. 11. However, the X-ray detector of this modification may also be applied to the configurations of the first, second, and third embodiments. In addition, the light blocking wall 17 of the scintillator panel 9 may be omitted as well while the light blocking walls 21 are provided in the scintillator panel 13. In this configuration, it is possible to simplify the apparatus configuration and provide the X-ray detector with a lower cost.

(9) In the configuration of the embodiments described above, the arrangement pitch of the light blocking walls 17 provided in the scintillator panel 9 is equal to the arrangement pitch of the light blocking walls 21 provided in the scintillator panel 13. However, the invention is not limited thereto. As illustrated in FIG. 20, the arrangement pitch of the light blocking walls 17 may be different from the arrangement pitch of the light blocking walls 21. In this case, the arrangement pitch of the scintillator elements 15 and the arrangement pitch of the pixels 25 become equal to the arrangement pitch of the light blocking walls 17. Similarly, the arrangement pitch of the scintillator elements 19 and the arrangement pitch of the pixels 29 become equal to the arrangement pitch of the light blocking walls 21. Therefore, the arrangement pitch of the pixels 25 becomes different from the arrangement pitch of the pixels 29.

In particular, when the arrangement pitch of the light blocking walls 21 is larger than the arrangement pitch of the light blocking walls 17, it is possible to arrange the light blocking walls 21 on straight lines obtained by linking an X-ray focal point p of the X-ray source and the light blocking walls 17 as illustrated in FIG. 20. When the X-rays spread radially, the spreading of the X-rays transmitting through the scintillator panel 13 becomes wider than the spreading of the X-rays transmitting through the scintillator panel 9. Therefore, in FIG. 20, considering this fact, the near-side scintillator panel 9 has a narrower width to match the beam width of the X-ray, and the far-side scintillator panel 13 has a wider width. Similarly, the arrangement pitch of the light blocking walls 17 is narrower to match the beam width of the X-rays, and the arrangement pitch of the light blocking walls 21 is wider. FIG. 20 illustrates a case where this modification is applied to the configuration of the second embodiment. Therefore, assuming that the X-ray beams spread radially, the light blocking walls 21 of the scintillator panel 13 are arranged to extend from the light blocking walls 17 of the scintillator panel 9. For convenient description purposes, the X-ray detector according to this modification corresponds to the X-ray detector according to the fourth embodiment of FIG. 11. Alternatively, the X-ray detector according to this modification may also be applied to other configurations of the first, second, and third embodiments.

(10) In the configuration of the modification 9 described above, the arrangement pitch of the pixels 25 is different from the arrangement pitch of the pixels 29. However, the arrangement pitches may be equal to each other. The arrangement pitch of the light blocking walls may be changed while the arrangement pitch of the pixels is constant. FIG. 21 illustrates an example in which the arrangement pitch of the light blocking walls 21 is changed. An upper part of FIG. 21 illustrates a case where the light blocking walls 21 are arranged as described in the aforementioned embodiments. A middle part of FIG. 21 illustrates a case where the light blocking walls 21 deviates to the right side.

In this case, the light blocking wall 21 deviates to the right side from the state of the upper part of FIG. 21 by a shift amount smaller than a half of the thickness of the light blocking wall 21. By setting the shift amount of the light blocking wall 21 to be smaller than a half of the thickness of itself, it is possible to retain an optical insulation property of a pair of pixels 29 around the light blocking wall 21. That is, even when the light blocking wall 21 is shifted as illustrated in the middle part of FIG. 21, fluorescent light generated in the scintillator element 15 positioned in the left side of the shifted light blocking wall 21 is blocked by the light blocking wall 21, so that it is not incident to the pixels 29 positioned in the right side of the light blocking wall 21. In addition, fluorescent light generated in the scintillator element 15 positioned in the right side of the shifted light blocking wall 21 is blocked by the light blocking wall 21, so that it is not incident to the pixels 29 positioned in the left side of the light blocking wall 21. Note that, as the light blocking wall 21 is shifted, the width between the scintillator elements 15 positioned in both sides of the light blocking wall 21 is changed.

That is, the scintillator element 15 positioned in the right side of the shifted light blocking wall 21 has a narrower width, and the scintillator element 15 positioned in the left side of the shifted light blocking wall 21 has a wider width. In this manner, the scintillator elements 15 of this modification do not have the same width. Note that the arrangement pitch of the scintillator elements 15 is constant across the scintillator panels 13. The ratio between the pitch of the light blocking walls 17 and the pitch of the light blocking walls 21 according to this modification is equal to a ratio between the spreading width obtained when radiation beams spreading radially from a radiation source reach the light blocking wall 17 and the spreading width obtained when the radiation beams reach the light blocking wall 21.

The lower part of FIG. 21 illustrates a state in which the light blocking wall 21 deviates to the left side. In this case, the light blocking wall 21 deviates to the left side from the state of the upper part of FIG. 21 by a shift amount smaller than a half of the thickness of the light blocking wall 21. Similar to the middle part of FIG. 21, by setting the shift amount of the light blocking wall 21 to be smaller than a half of the thickness of itself, it is possible to retain an optical insulation property of a pair of pixels 29 around the light blocking wall 21. Note that, as the light blocking wall 21 is shifted, the width between the scintillator elements 15 positioned in both sides of the light blocking wall 21 is changed. That is, the scintillator element 15 positioned in the right side of the shifted light blocking wall 21 has a wider width, and the scintillator element 15 positioned in the left side of the shifted light blocking wall 21 has a narrower width.

While an example in which the light blocking wall 21 of the scintillator panel 13 is shifted in the arrangement direction of the light blocking walls 21 has been described with reference to FIG. 21, the light blocking wall 17 of the scintillator panel 9 may also be shifted in the arrangement direction of the light blocking walls 17.

According to this modification, while the arrangement pitch of the pixels 25 of the scintillator panel 9 is equal to the arrangement pitch of the pixels 29 of the scintillator panel 13, the arrangement pitch of the light blocking walls 17 may be different from the arrangement pitch of the light blocking walls 19. As a result, it is possible to provide an X-ray detector obtained by considering a fact that the X-rays spread radially as described above in conjunction with FIG. 20. The pitch of the light blocking walls 21 according to this modification is different depending on the position of the scintillator panel 13.

(11) The light blocking walls 17 and 21 according to the invention may be manufactured through X-ray lithography (LIGA).

(12) In each of the embodiments described above, the neighboring pixels are bonded to each other in their ends. However, the invention is not limited thereto. As illustrated in FIG. 22, the light blocking wall 21 may extend to the side face of the pixel 29. In this manner, it is possible to reliably optically partition the neighboring pixels 29. While FIG. 22 illustrates an example in which the light blocking wall 21 of the scintillator panel 13 extends to the side face of the pixel 29, the light blocking wall 17 of the scintillator panel 9 may also extend to the side face of the pixel 25. The pixels according to the invention are placed in the cells formed by the grid of the light blocking walls 21. Note that, although the X-ray detector according to this modification corresponds to the X-ray detector according to the fourth embodiment described above in conjunction with FIG. 11 for convenient description purposes, the X-ray detector according to this modification may also be applied to other configurations of the first, second, and third embodiments.

(13) In the embodiments described above, the light blocking walls are arranged in parallel with each other. However, the invention is not limited thereto. As illustrated in FIG. 23, the light blocking walls may be configured to be gradually inclined from a center of the scintillator panel 9 to its end portions. In the case of FIG. 23, the light blocking walls 17 and 21 extend along straight lines passing through the focal point p of the X-ray source. As a result, X-rays are not detected in both neighboring pixels. Therefore, it is possible to provide an X-ray detector having a high spatial resolution. Note that the apparatus of FIG. 23 has a configuration corresponding to the fourth embodiment in which the light blocking walls 21 are arranged to extend from the light blocking walls 17. According to this modification, such a configuration may be applied to other configurations of the first, second, and third embodiments. The light blocking walls 17 and 21 according to the invention are configured to be gradually inclined from the center of the grid to the end portions.

(14) Application of the X-ray detector according to the invention is not limited to the dual energy imaging. In order to obtain a clear X-ray image applicable to other imaging applications such as a nondestructive inspection, it is desirable to arrange the X-ray grid on a detection surface of the X-ray detector to remove scattering X-rays generated from an inspection target or influence of diffraction phenomena caused by crystals contained in an inspection target. However, in the case of the nondestructive inspection, a distance between the X-ray focal point and the X-ray detector changes whenever the imaging is performed in many cases. Therefore, it is difficult to arrange the X-ray grid. In this regard, a clear X-ray image can be obtained by using the scintillator panel 9 corresponding to the first layer of the X-ray detector according to the invention instead of the X-ray grid and using the scintillator panel 13 corresponding to the second layer to create the X-ray image. In this case, the X-ray image obtained by removing scattering X-rays or influence of diffraction phenomena can be obtained from a detection result of the scintillator panel 13 corresponding to the second layer. It is possible to obtain an image having the same sensitivity as that of the related art at the same time by combining the first and second layers.

(15) The X-ray detector according to the invention may be applicable to both dual energy imaging in which irradiation of high-energy X-rays and irradiation of low-energy X-rays are alternately repeated and dual energy imaging executed by irradiating high-energy X-rays and low-energy X-rays simultaneously.

DESCRIPTION OF REFERENCE NUMERALS AND SIGNS

1 X-ray detector
3 scintillator block
5, 7 photodetection panel
9, 13 scintillator panel
11 substrate
15, 19 scintillator element
17, 21 light blocking wall
25, 29 pixel
31, 33 panel assembly
35 scintillator assembly

The invention claimed is:

1. An X-ray detector comprising:
a first scintillator panel provided with a first light blocking portion and a first scintillator element filled in each cell partitioned by the first light blocking portion in a two-dimensional matrix shape to convert low-energy X-rays out of incident X-rays into light;
a second scintillator panel provided with a second light blocking portion and a second scintillator element filled in each cell partitioned by the second light blocking portion in a two-dimensional matrix shape to convert high-energy X-rays having higher energy than that of the low-energy X-rays out of the incident X-rays into light;
a first photodetection panel provided with photoelectric conversion elements arranged in a two-dimensional matrix shape to convert the light converted by the first scintillator element into electric charges; and
a second photodetection panel provided with photoelectric conversion elements arranged in a two-dimensional matrix shape to convert the light converted by the second scintillator element into electric charges,
wherein each of the first and second scintillator panels and the first and second photodetection panels is stacked in an X-ray incidence direction;
a grid pattern of the first light blocking portion and a grid pattern of the second light blocking portion deviate in a vertical and horizontal direction from each other along the X-ray incidence face; and
the scintillator element of the second scintillator panel is arranged to deviate in the vertical and the horizontal directions from a position linked to the scintillator element of the first scintillator panel.

2. The X-ray detector according to claim 1, wherein a pitch of the second light blocking portion is larger than a pitch of the first light blocking portion.

3. The X-ray detector according to claim 2, wherein a ratio between the pitch of the first light blocking portion and the pitch of the second light blocking portion is equal to a ratio between a spreading width obtained when radiation beams spreading radially from a radiation source reach the first light blocking portion and a spreading width obtained when the radiation beams reach the second light blocking portion.

4. The X-ray detector according to claim 1, further comprising a planar substrate, wherein the first scintillator panel is formed on one surface of the substrate, and the second scintillator panel is formed on the other surface of the substrate.

5. The X-ray detector according to claim 1, wherein the first photodetection panel, the first scintillator panel, the second scintillator panel, and the second photodetection panel are stacked sequentially in this order, and
the first scintillator panel and the second scintillator panel are directly stacked.

6. The X-ray detector according to claim 1, wherein the first scintillator panel, the first photodetection panel, the second scintillator panel, and the second photodetection panel are stacked sequentially in this order.

7. The X-ray detector according to claim 1, wherein a pitch of the light blocking portion is different depending on a position of the light blocking portion.

8. The X-ray detector according to claim 1, wherein the photoelectric conversion element is placed inside a partition formed by the grid pattern of the light blocking portion.

9. The X-ray detector according to claim 1, wherein a light blocking wall included in the grid pattern of the light blocking portion is gradually inclined from a center of the grid pattern to an end portion.

* * * * *